(12) United States Patent
Huh et al.

(10) Patent No.: US 9,310,779 B2
(45) Date of Patent: Apr. 12, 2016

(54) MOBILE TERMINAL AND CONTROLLING METHOD THEREOF

(71) Applicants: Jiyoung Huh, Seoul (KR); Myungeun Park, Seoul (KR); Seungbum Hong, Seoul (KR)

(72) Inventors: Jiyoung Huh, Seoul (KR); Myungeun Park, Seoul (KR); Seungbum Hong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 83 days.

(21) Appl. No.: 13/957,866

(22) Filed: Aug. 2, 2013

(65) Prior Publication Data

US 2014/0269224 A1    Sep. 18, 2014

(30) Foreign Application Priority Data

Mar. 15, 2013 (KR) .................. 10-2013-0027754

(51) Int. Cl.

| | |
|---|---|
| G04G 21/02 | (2010.01) |
| G04G 13/02 | (2006.01) |
| A61B 5/00 | (2006.01) |
| H04M 1/725 | (2006.01) |
| A61B 5/024 | (2006.01) |
| A61B 5/026 | (2006.01) |
| A61B 5/0402 | (2006.01) |
| A61B 5/0476 | (2006.01) |
| A61B 5/0488 | (2006.01) |
| A61B 5/145 | (2006.01) |

(52) U.S. Cl.
CPC ............ G04G 21/025 (2013.01); A61B 5/4806 (2013.01); G04G 13/021 (2013.01); *A61B 5/024* (2013.01); *A61B 5/026* (2013.01); *A61B 5/0402* (2013.01); *A61B 5/0476* (2013.01); *A61B 5/0488* (2013.01); *A61B 5/14542* (2013.01); *H04M 1/72522* (2013.01); *H04M 2250/12* (2013.01)

(58) Field of Classification Search
CPC ........................ G04G 13/021; G04G 21/025
USPC ..................... 368/73; 340/575, 576
See application file for complete search history.

(56) References Cited

U.S. PATENT DOCUMENTS

| | | | | |
|---|---|---|---|---|
| 4,228,806 | A | * | 10/1980 | Lidow ............................ 600/544 |
| 4,894,813 | A | * | 1/1990 | Pacher et al. ................. 368/256 |
| 5,101,831 | A | * | 4/1992 | Koyama et al. ............... 600/500 |

(Continued)

FOREIGN PATENT DOCUMENTS

| | | |
|---|---|---|
| EP | 1 855 170 A2 | 11/2007 |
| JP | 2009-232925 A | 10/2009 |
| WO | WO 2011/027266 A1 | 3/2011 |

OTHER PUBLICATIONS

European Search Report issued in Application No. 13006054.4 dated Oct. 29, 2014.

*Primary Examiner* — Amy Cohen Johnson
*Assistant Examiner* — Jason Collins
(74) *Attorney, Agent, or Firm* — Ked & Associates, LLP

(57) ABSTRACT

A terminal and a method of controlling the same are disclosed, by which a snooze function for an alarm can be activated depending on whether a user sleeps after outputting the alarm. The terminal may include a measuring unit configured to measure a bio-information of a user, a memory having an alarm set therein, an alarm unit configured to output the alarm, and a controller configured to measure the bio-information of the user through the measuring unit after the outputted alarm. The controller, when determining that the user is currently asleep based on the measured bio-information, may control a snooze function for the alarm to be automatically activated.

19 Claims, 21 Drawing Sheets

(56) References Cited

U.S. PATENT DOCUMENTS

| | | | |
|---|---|---|---|
| 5,524,101 A * | 6/1996 | Thorgersen et al. | 368/10 |
| 5,846,206 A * | 12/1998 | Bader | 600/534 |
| 5,928,133 A * | 7/1999 | Halyak | 600/26 |
| 6,477,117 B1 * | 11/2002 | Narayanaswami et al. | 368/251 |
| 6,678,215 B1 * | 1/2004 | Treyz et al. | 368/10 |
| 6,888,779 B2 * | 5/2005 | Mollicone et al. | 368/10 |
| 7,248,915 B2 * | 7/2007 | Ronnholm | 600/544 |
| 7,468,934 B1 * | 12/2008 | Janik | 368/13 |
| 7,608,041 B2 * | 10/2009 | Sutton | 600/300 |
| 2003/0095476 A1 * | 5/2003 | Mollicone et al. | 368/250 |
| 2003/0142591 A1 | 7/2003 | Baweja et al. | |
| 2003/0231551 A1 * | 12/2003 | Saylor et al. | 368/10 |
| 2005/0249049 A1 * | 11/2005 | Jarrett et al. | 368/250 |
| 2006/0293608 A1 * | 12/2006 | Rothman et al. | 600/545 |
| 2007/0189124 A1 * | 8/2007 | Cuisinier | 368/73 |
| 2008/0062819 A1 * | 3/2008 | Kelly et al. | 368/11 |
| 2008/0186808 A1 * | 8/2008 | Lee | 368/10 |
| 2012/0007737 A1 | 1/2012 | Kangas et al. | |
| 2012/0120773 A1 * | 5/2012 | O'Toole | 368/73 |
| 2014/0269223 A1 * | 9/2014 | Mokhnatkina et al. | 368/73 |

* cited by examiner

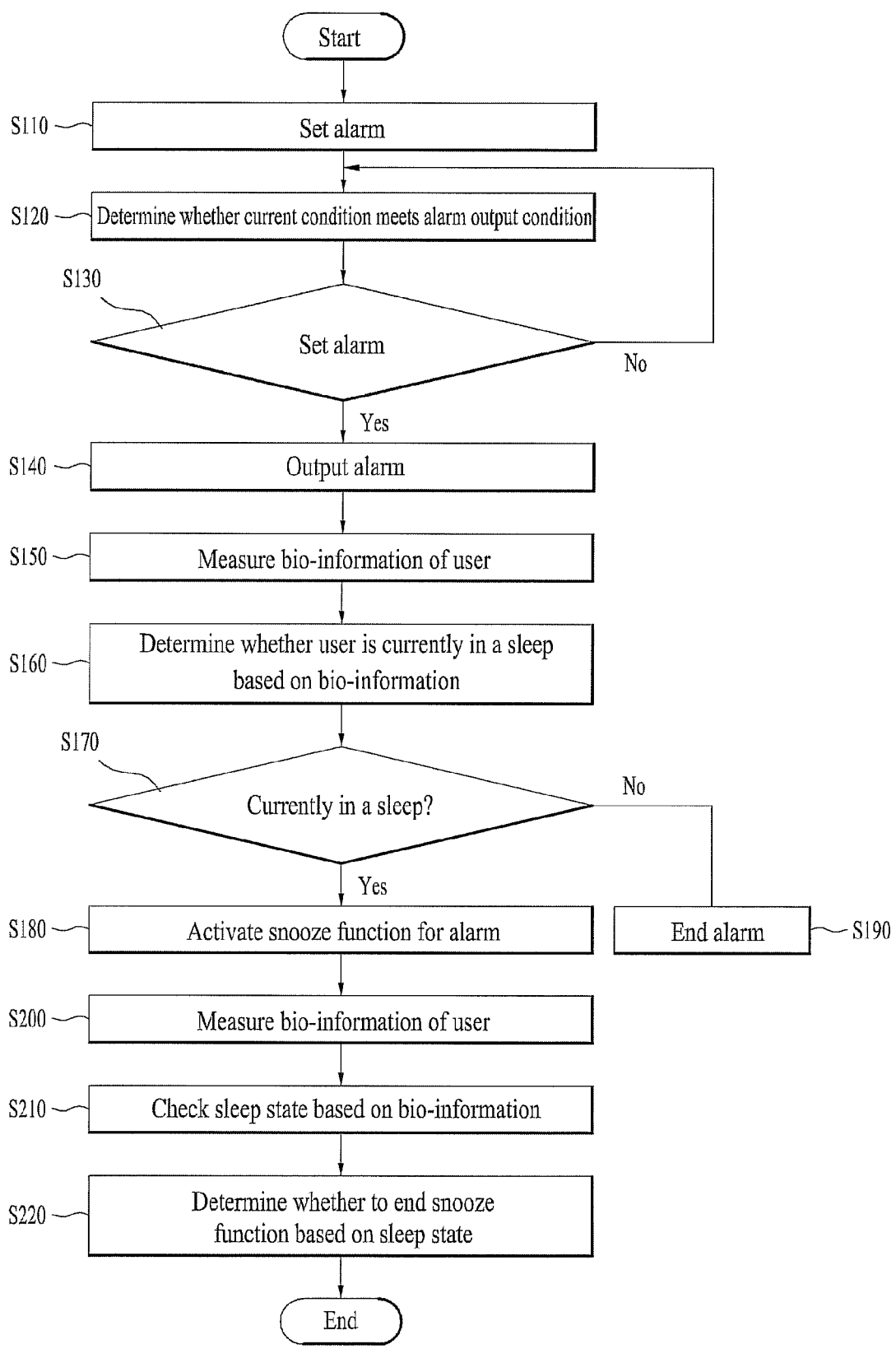

Repetitive interval:
changed 5 minutes to 7 minutes

Repetitive interval:
changed 5 minutes to 3 minutes

Repetitive count:
changed 5 times to 7 times

Repetitive count:
changed 5 times to 3 times

Alarm sound:
changed audio to vibration sound

Alarm sound:
changed vibration sound to audio

Repetitive interval:
changed 5 minutes to 7 minutes

Repetitive interval:
changed 5 minutes to 3 minutes

MOBILE TERMINAL AND CONTROLLING METHOD THEREOF

CROSS-REFERENCE TO RELATED APPLICATION(S)

This application claims priority under 35 U.S.C. §119 to Korean Application No. 10-2013-0027754 filed in Korea on Mar. 15, 2013, whose entire disclosure(s) is/are hereby incorporated by reference.

BACKGROUND

1. Field

The present disclosure relates to a mobile terminal, and more particularly, to a mobile terminal and a method of controlling the mobile terminal.

2. Background

Mobile terminals and methods of controlling the same are known. However, they suffer from various disadvantages.

BRIEF DESCRIPTION OF THE DRAWINGS

The accompanying drawings, which are included to provide a further understanding of the disclosure and are incorporated in and constitute a part of this application, illustrate embodiment(s) of the disclosure and together with the description serve to explain the principle of the disclosure. The above and other aspects, features, and advantages of the present disclosure will become more apparent upon consideration of the following description of preferred embodiments, taken in conjunction with the accompanying drawing figures. In the drawings:

FIG. 5 is a flowchart of a process for providing a snooze function in accordance with a sleep state of a user after an alarm output according to the present disclosure;

DETAILED DESCRIPTION

Figure 1:
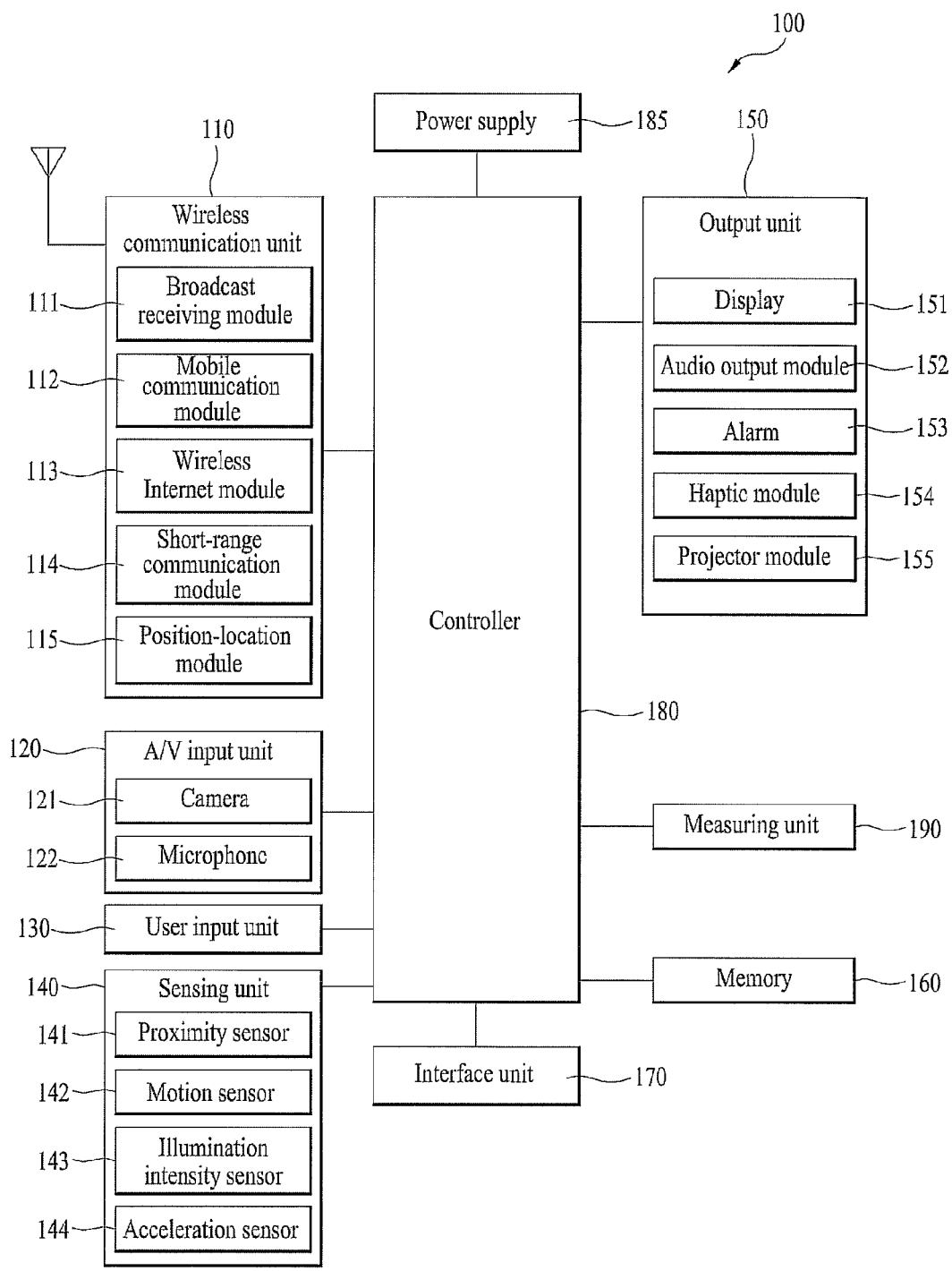
FIG. 1 is a block diagram of a terminal according to the present disclosure.

In the following detailed description, reference is made to the accompanying drawing figures which form a part hereof, and which show by way of illustration specific embodiments of the disclosure. It is to be understood by those of ordinary skill in this technological field that other embodiments may be utilized, and structural, electrical, as well as procedural changes may be made without departing from the scope of the present disclosure. Wherever possible, the same reference numbers will be used throughout the drawings to refer to the same or similar parts.

The terms "module," "unit," and "part" are used herein with respect to various elements only to facilitate disclosure of the disclosure. Therefore, the terms "module," "unit," and "part" are used interchangeably herein.

A mobile terminal is a device that can be configured to perform various functions, such as data and voice communications, capturing still images and video via a camera, recording audio, playing music files and outputting music via a speaker system, and displaying images and video on a display. Some terminals include additional functionality to support game playing, while other terminals are also configured as multimedia players. More recently, mobile terminals have been configured to receive broadcast and multicast signals to permit viewing of content, such as videos and television programs.

Generally, terminals can be classified into mobile terminals and stationary terminals according to a presence or nonpresence of mobility. And, the mobile terminals can be further classified into handheld terminals and vehicle mount terminals according to availability for hand-carry.

There are ongoing efforts to support and increase the functionality of mobile terminals. Such efforts include software and hardware improvements, as well as changes and improvements in the structural components which form the mobile terminal.

Recently, a mobile terminal tends to be implemented into a wearable device type such as a user-wearable wristwatch type, a user-wearable eyeglass type, a user-wearable necklace type and the like. A user wears a mobile terminal of a wearable device type to enjoy unique functions of a wrist watch, eyeglasses, a necklace and the like as well as functions of the mobile terminal.

Meanwhile, a mobile terminal provides an alarm function of outputting an alarm sound on a user-set time. Using the alarm function, a user can recognize an important schedule hour or wake up from sleep on a desired hour.

Many ongoing efforts have been made to newly add a repetitive alarm function to an alarm function of a related art. For example, there is a snooze function applicable together with a general alarm function of outputting an alarm sound once on a set alarm hour.

The snooze function means a function of outputting an alarm sound repeatedly by preset repetition periods and at a count of repetitions after outputting the alarm sound in accordance with an alarm function.

In particular, although a user cancels an alarm function unintentionally despite waking up fully from sleep, the user can wake up from the sleep on a user-intended hour through the snooze function.

However, if a fully-awakened user is unable to automatically recognize whether the snooze function is turned on, it is inconvenient for the user to manually manipulate the cancellation of the snooze function.

Accordingly, embodiments of the present disclosure are directed to a mobile terminal and controlling method thereof that substantially obviate one or more problems due to limitations and disadvantages of the related art.

An object of the present disclosure is to provide a terminal and controlling method thereof, by which a snooze function for an alarm can be activated depending on whether a user sleeps after outputting the alarm.

Additional advantages, objects, and features of the disclosure will be set forth in the disclosure herein as well as the accompanying drawings. Such aspects may also be appreciated by those skilled in the art based on the disclosure herein.

The present disclosure can be applied to various types of terminals. For example, the terminals can include mobile terminals as well as stationary terminals, such as mobile phones, user equipments, smart phones, digital televisions (DTVs), computers, digital broadcast terminals, personal digital assistants, portable multimedia players (PMP) and navigators.

In a terminal described in the present specification, the mobile terminal can be configured as a wearable device type, which is wearable on a part of a user's body, such as a wrist watch type, an eyeglass type, a necklace type and the like. In this case, the mobile terminal may have a configuration detachable from a wristwatch, eyeglasses, a ring, a necklace or the like. Alternatively, the mobile terminal may have a configuration built in one body of a wristwatch, eyeglasses, a ring, a necklace or the like.

For ease of description, the present disclosure will be described with respect to a mobile terminal 100 shown in FIGS. 1 through 2B. However, it should be understood that the present disclosure can also be applied to other types of terminals.

FIG. 1 illustrates an exemplary block diagram of the mobile terminal 100 in accordance with one embodiment of the present disclosure. It should be understood that embodiments, configurations and arrangements other than that depicted in FIG. 1 can be used without departing from the spirit and scope of the disclosure. As shown in FIG. 1, the mobile terminal 100 includes a wireless communication unit 110, an audio/video (AV) input unit 120, a user input unit 130, a sensing unit 140, an output unit 150, a memory 160, an interface unit 170, a controller 180, and a power supply unit 190. It should be understood that the mobile terminal 100 may include additional or fewer components than those shown in FIG. 1.

The wireless communication unit 110 can include one or more components for allowing wireless communication between the mobile terminal 100 and a wireless communication system or network within which the mobile terminal 100 is located.

Moreover, the wireless communication unit 110 of the present disclosure can receive bio-information of a user from an external measurement device for measuring the bio-information of the user. In this case, the bio-information of the user may include at least one or two of a blood pressure, a pulse, a body temperature, an electrocardiogram, an electromyogram, an electroencephalogram, a blood flow, an oxygen saturation and the like.

For example, the wireless communication unit 110 can include a broadcast receiving module 111, a mobile communication module 112, a wireless Internet module 113, a short-range communication module 114, and a position-location module 115.

The broadcast receiving module 111 receives a broadcast signal and/or broadcast related information from an external broadcast management server via a broadcast channel. In one embodiment, the mobile terminal 100 can be configured to include two or more broadcast receiving modules 111 to enable simultaneous reception of two or more broadcast channels or to facilitate switching of broadcast channels.

The broadcast channel can include a satellite channel and a terrestrial channel. The broadcast management server can be a server that generates and transmits a broadcast signal and/or broadcast related information, or a server that receives a previously-generated broadcasting signal and/or previously-generated broadcasting-related information and transmits the previously-generated broadcast signal and/or previously-generated broadcasting-related information to the mobile terminal 100.

For example, the broadcast signal can be implemented as a TV broadcast signal, a radio broadcast signal, a data broadcast signal, and various other types of signals. In one embodiment, the broadcast signal can include a combination of the broadcast signal and a TV broadcast signal or a combination of the broadcast signal and a radio broadcast signal.

The broadcast-related information can include broadcast channel information, broadcast program information, or broadcast service provider information. The broadcast-related information can be provided to the mobile terminal 100 through a mobile communication network. In such a case, the broadcast-related information can be received by the mobile communication module 112.

The broadcast-related information can be implemented in various forms. For example, the broadcast-related information can have the form of an electronic program guide (EPG)

of the digital multimedia broadcasting (DMB) standard, or an electronic service guide (ESG) of the digital video broadcast-handheld (DVB-H) standard.

The broadcast receiving module 111 can be configured to receive broadcast signals transmitted from various types of broadcast systems, such as digital multimedia broadcasting-terrestrial (DMB-T), digital multimedia broadcasting-satellite (DMB-S), DVB-H, digital video broadcast-convergence of broadcast and mobile services (DVB-CBMS), Open Mobile Alliance broadcast (OMA-BCAST), the data broadcasting system known as media forward link only (MediaFLO) and integrated services digital broadcast-terrestrial (ISDB-T) systems. The broadcast receiving module 111 can be configured to receive signals from broadcasting systems providing broadcasting signals other than the above-described digital broadcasting systems. The broadcast signal and/or broadcast-related information received via the broadcast receiving module 111 can be stored in a storage medium, such as the memory 160.

The mobile communication module 112 can transmit and/or receive wireless signals to and/or from at least one network entity, such as a base station, an external terminal, or a server. For example, such wireless signals can include audio, video, and data according to a transmission and reception of text/multimedia messages.

Moreover, the mobile communication module 112 of the present disclosure can receive bio-information of a user from an external measurement device for measuring the bio-information of the user. In this case, the bio-information of the user may include at least one of a blood pressure, a pulse, a body temperature, an electrocardiogram, an electromyogram, an electroencephalogram, a blood flow, an oxygen saturation and the like.

The wireless Internet module 113 can be a module that supports Internet access for the mobile terminal 100. For example, the wireless Internet module 113 can be included in the mobile terminal 100 or installed in an external device that is coupled to the mobile terminal 100. For example, the wireless Internet technology implemented by the wireless Internet module 113 can be a wireless local area network (WLAN), Wi-Fi, Wireless Broadband (WiBro), World Interoperability for Microwave Access (WiMAX), or High Speed Downlink Packet Access (HSDPA).

Moreover, as mentioned in the foregoing description, the wireless internet module 113 can receive or download the data relevant to the area, in which the mobile terminal 100 is located, from the external server.

Moreover, the wireless internet module 113 of the present disclosure is connected to communicate with an external measurement device for measuring the bio-information of the user and can receive the bio-information of the user from the external measurement device. In this case, the bio-information of the user may include at least one of a blood pressure, a pulse, a body temperature, an electrocardiogram, an electromyogram, an electroencephalogram, a blood flow, an oxygen saturation and the like.

The short-range communication module 114 can be a module for supporting relatively short-range communications. For example, the short-range communication module 114 can be configured to communicate using short range communication technology, such as, radio frequency identification (RFID), Infrared Data Association (IrDA), or Ultra-wideband (UWB), as well as networking technologies, such as Bluetooth or ZigBee.

Moreover, the short range communication module 114 of the present disclosure is connected to short-range communicate with an external measurement device for measuring the bio-information of the user and can receive the bio-information of the user from the external measurement device. In this case, the bio-information of the user may include at least one of a blood pressure, a pulse, a body temperature, an electrocardiogram, an electromyogram, an electroencephalogram, a blood flow, an oxygen saturation and the like.

The position-location module 115 identifies or otherwise obtains the location of the mobile terminal 100. In one embodiment, the position-location module 115 can include a global positioning system (GPS) module.

The A/V input unit 120 can be used to input an audio signal or a video signal, and can include a camera 121 and a microphone 122. For example, the camera 121 can have a digital zoom feature and can process image frames of still images or video obtained by an image sensor of the camera 121 in a video call mode or a photographing mode. The processed image frames can be displayed on a display unit 151.

The image frames processed by the camera 121 can be stored in the memory 160 or can be externally transmitted via the wireless communication unit 110. Optionally, at least two cameras 121 can be provided to the mobile terminal 100 according to environment of usage.

The microphone 122 can receive an external audio signal while operating in a particular mode, such as a phone call mode, a recording mode or a voice recognition mode, and can process the received audio signal into electrical audio data. The audio data can then be converted into a form that can be transmitted to a mobile communication base station through the mobile communication module 112 in the call mode. The microphone 122 can apply various noise removal or noise canceling algorithms for removing or reducing noise generated when the external audio signal is received.

The user input unit 130 can generate input data in response to user manipulation of a corresponding input device or devices, such as a keypad, a dome switch, a touchpad, a jog wheel, or a jog switch. In one embodiment, the touchpad can be configured as a static pressure or capacitance type.

The sensing unit 140 can sense a change of position of the mobile terminal 100 or a component of the mobile terminal 100, relative positioning of components of the mobile terminal 100, such as a display and keypad, whether a user touches the mobile terminal 100, an orientation of the mobile terminal 100, acceleration or deceleration of the mobile terminal 100, and a current state of the mobile terminal 100, such as an open or close state. The sensing unit 140 can also include a proximity sensor 141.

The sensing unit 140 senses such a current state of the terminal 100 as an open/closed state of the terminal 100, a location of the terminal 100, a presence or non-presence of a contact with a user, a direction (e.g., azimuth, etc.) of the terminal 100, a measured motion size of the terminal 100, a surrounding illumination intensity of the terminal 100, an acceleration/deceleration of the terminal 100 and the like and then generates a sensing signal for controlling an operation of the terminal 100.

The sensing unit 140 may include a proximity sensor 141, a motion sensor 142, an illumination intensity sensor 143 and an acceleration sensor 144. The proximity sensor 141 shall be described in detail later.

The motion sensor 142 senses a motion gesture or size of the terminal 100 moved by a user and then outputs the sensed motion gesture or size. The illumination intensity sensor 143 measures a surrounding illumination intensity of the terminal 100 and then outputs the measured surrounding illumination intensity. The acceleration sensor 144 measures acceleration/deceleration of the terminal 100 and then outputs the measured acceleration/deceleration.

The output unit 150 can generate visual, auditory and/or tactile outputs and can include the display unit 151, an audio output module 152, an alarm unit 153, a haptic module 154, and a projector module 155. The display unit 151 can be configured to display information processed by the mobile terminal 100.

For example, when the mobile terminal 100 is in a call mode, the display unit 151 can display a user interface (UI) or a graphic user interface (GUI) for placing, conducting, and terminating a call. For example, when the mobile terminal 100 is in the video call mode or the photographing mode, the display unit 151 can additionally or alternatively display images which are associated with such modes, the UI or the GUI.

The display unit 151 can be implemented using display technologies including, for example, a liquid crystal display (LCD), a thin film transistor-liquid crystal display (TFT-LCD), an organic light-emitting diode display (OLED), a flexible display and a three-dimensional display. The mobile terminal 100 can be configured to include more than one display unit 151 according to the configuration of the mobile terminal 100.

For example, the mobile terminal 100 can include a number of display units 151 that are arranged on a single face of the mobile terminal 100, and can be spaced apart from one another or integrated in one body. The number of display units 151 can also be arranged on different sides of the mobile terminal 100.

In one embodiment, the display used in the display unit 151 can be of a transparent type or a light transmittive type, such that the display unit 151 is implemented as a transparent display. For example, the transparent display can include a transparent OLED (TOLED) display. The rear structure of the display unit 151 can also be of a light transmittive type. Accordingly, a user may see an object located behind the body of the mobile terminal 100 through the transparent area of the body of the mobile terminal 100 that is occupied by the display unit 151.

When the display unit 151 and a sensor for sensing a user touch (hereinafter referred to as a "touch sensor") are configured as a layered structure to form a touch screen, the display unit 151 can be used as an input device in addition to an output device. For example, the touch sensor can be in the form of a touch film, a touch sheet, or a touch pad.

The touch sensor can convert a variation in pressure applied to a specific portion of the display unit 151 or a variation in capacitance generated at a specific portion of the display unit 151 into an electric input signal. The touch sensor can sense pressure resulting from a touch, as well as the position and area of the touch.

When the user applies a touch input to the touch sensor, a signal corresponding to the touch input can be transmitted to a touch controller (not shown). The touch controller can process the signal and transmit data corresponding to the processed signal to the controller 180. The controller 180 can then use the data to detect a touched portion of the display unit 151.

The proximity sensor 141 of the sensing unit 140 can be located in an internal region of the mobile terminal 100 and either enclosed by the touch screen or around the touch screen. The proximity sensor 141 can sense an object approaching a prescribed detecting surface or an object located near the proximity sensor 141 without any physical contact using an electromagnetic field or infrared rays. The longevity of the proximity sensor 141 can substantially exceed the longevity of a contact sensor and, therefore, can have wide applications in the mobile terminal 100.

The proximity sensor 141 can include a transmittive photo-electric sensor, a direct reflection photo-electric sensor, a mirror reflection photo-electric sensor, a radio frequency oscillation proximity sensor, an electrostatic capacity proximity sensor, a magnetic proximity sensor, and/or an infrared proximity sensor. In one embodiment, the touch screen can include an electrostatic capacity proximity sensor, such that a proximity of a pointer can be detected through a variation in an electric field according to the proximity of the pointer. Accordingly, the touch screen or touch sensor can be classified as the proximity sensor 141.

For purposes of clarity, an action of the pointer approaching the touch screen and being recognized without actually contacting the touch screen will be herein referred to as a "proximity touch," while an action of bringing the pointer into contact with the touch screen will be herein referred to as a "contact touch." A proximity touch position of the pointer on the touch screen can correspond to a position on the touch screen from which the pointer is situated perpendicularly with respect to the touch screen.

Via the proximity sensor 141, a proximity touch and a proximity touch pattern, such as a proximity touch distance, a proximity touch duration, a proximity touch position, or a proximity touch movement state can be detected. For example, information corresponding to the detected proximity touch action and proximity touch pattern can be displayed on the touch screen.

The audio output module 152 can output audio data received from the wireless communication unit 110, or stored in the memory 160, in a call receiving mode, a call placing mode, a recording mode, a voice recognition mode, or a broadcast receiving mode. The audio output module 152 can also provide audio signals related to particular functions performed by the mobile terminal 100, such as a call received or a message received. For example, the audio output module 152 can include a speaker, a buzzer, or other audio output device.

The alarm unit 153 can output a signal for indicating the occurrence of an event of the mobile terminal 100, such as a call received event, a message received event and a touch input received event, using a vibration as well as video or audio signals. The video or audio signals can also be output via the display unit 151 or the audio output module 152. Therefore, in various embodiments, the display unit 151 or the audio output module 152 can be considered as a part of the alarm unit 153.

The haptic module 154 can generate various tactile effects that can be physically sensed by the user. For example, a tactile effect generated by the haptic module 154 can include vibration. The intensity and/or pattern of the vibration generated by the haptic module 154 can be controlled. For example, different vibrations can be combined and provided or sequentially provided.

The haptic module 154 can generate a variety of tactile effects in addition to a vibration. Such tactile effects include an effect caused by an arrangement of vertically moving pins that are in contact with the skin of the user; an effect caused by a force of air passing through an injection hole or a suction of air through a suction hole; an effect caused by skimming over the user's skin; an effect caused by contact with an electrode; an effect caused by an electrostatic force; and an effect caused by the application of cold and warm temperatures using an endothermic or exothermic device.

For example, the haptic module 154 can enable a user to sense the tactile effects through a muscle sense of the user's finger or arm, as well as to transfer the tactile effect through direct contact. Optionally, the mobile terminal 100 can include at least two haptic modules 154 according to the configuration of the mobile terminal 100.

The projector module 155 is an element for performing an image projection function of the mobile terminal 100. In one embodiment, the projector module 155 can be configured to display an image identical to or partially different from an image displayed by the display unit 151 on an external screen or wall according to a control signal of the controller 180.

For example, the projector module 155 can include a light source (not shown), such as a laser, that generates adequate light for external projection of an image, means for producing the image (not shown) to be projected via the light generated from the light source, and a lens (not shown) for enlarging the projected image according to a predetermined focus distance. The projector module 155 can further include a device (not shown) for adjusting the direction in which the image is projected by mechanically moving the lens or the entire projector module 155.

The projector module 155 can be classified as a cathode ray tube (CRT) module, a liquid crystal display (LCD) module, or a digital light processing (DLP) module according to a type of display used. For example, the DLP module operates by enabling the light generated from the light source to reflect on a digital micro-mirror device (DMD) chip and can advantageously reduce the size of the projector module 155.

The projector module 155 can preferably be configured in a lengthwise direction along a side, front or back of the mobile terminal 100. It should be understood, however, that the projector module 155 can be configured on any portion of the mobile terminal 100.

The memory 160 can store various types of data to support the processing, control, and storage requirements of the mobile terminal 100. For example, such types of data can include program instructions for applications operated by the mobile terminal 100, contact data, phone book data, messages, audio, still images, and/or moving images.

A recent use history or a cumulative usage frequency of each type of data can be stored in the memory unit 160, such as usage frequency of each phonebook, message or multimedia. Moreover, data for various patterns of vibration and/or sound output when a touch input is performed on the touch screen can be stored in the memory unit 160.

The memory 160 can be implemented using any type or combination of suitable volatile and non-volatile memory or storage devices, such as a flash memory, a hard disk type memory, a multimedia card micro type memory, a card type memory, such as a Secure Digital (SD) card or Extreme Digital (xD) card, a random access memory (RAM), a static random access memory (SRAM), a read-only memory (ROM), an erasable programmable read-only memory (EPROM), a programmable ROM (PROM), an electrically erasable programmable read-only memory (EEPROM), a magnetic memory, a magnetic disk, an optical disk, or other type of memory or data storage device. In other embodiments, the memory 160 can be a storage device that can be accessed by the mobile terminal 100 via the Internet.

The interface unit 170 can couple the mobile terminal 100 to external devices. The interface unit 170 can receive data from the external devices or power, and transmit the data or power to internal components of the mobile terminal 100. In addition, the interface unit 170 can transmit data of the mobile terminal 100 to the external devices. The interface unit 170 can include, for example, a wired or wireless headset port, an external charger port, a wired or wireless data port, a memory card port, a port for connecting a device having an identity module, an audio input/output (I/O) port, a video I/O port, and/or an earphone port.

The identity module is the chip for storing various kinds of information for authenticating the authority to use the mobile terminal 100. For example, the identity module can be a user identify module (UIM), a subscriber identify module (SIM) or a universal subscriber identify module (USIM). A device including the identity module (hereinafter referred to as "identity device") can also be manufactured in the form of a smart card. Therefore, the identity device can be connected to the mobile terminal 100 via a corresponding port of the interface unit 170.

When the mobile terminal 100 is connected to an external cradle, the interface unit 170 becomes a passage for supplying the mobile terminal 100 with a power from the cradle or a passage for delivering various command signals inputted from the cradle by a user to the mobile terminal 100. Each of the various command signals inputted from the cradle or the power can operate as a signal enabling the mobile terminal 100 to recognize that it is correctly loaded in the cradle.

Moreover, the interface unit 170 of the present disclosure is connected to an external measurement device for measuring the bio-information of the user and can receive the bio-information of the user from the external measurement device. In this case, the bio-information of the user may include at least one of a blood pressure, a pulse, a body temperature, an electrocardiogram, an electromyogram, an electroencephalogram, a blood flow, an oxygen saturation and the like.

The controller 180 can control the general operations of the mobile terminal 100. For example, the controller 180 can be configured to perform control and processing associated with voice calls, data communication, and/or video calls. The controller 180 can perform pattern recognition processing to recognize a character or image from a handwriting input or a picture-drawing input performed on the touch screen.

Moreover, the controller 180 can control all operations related to a start and end of a snooze function for alarm in response to alarm settings and a presence or non-presence of user's sleep according to the present disclosure.

The power supply unit 190 can be an external power source, an internal power source, or a combination thereof. The power supply unit 190 can supply power to other components in the mobile terminal 100.

Various embodiments described herein may be implemented in a computer-readable medium using, for example, computer software, hardware, or some combination thereof. For a hardware implementation, the embodiments described herein may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a selective combination thereof. Such embodiments may also be implemented by the controller 180.

For example, the procedures or functions described herein can be implemented in software using separate software modules that allow performance of at least one function or operation. Software codes can be implemented by a software application or program written in any suitable programming language. The software codes can be stored in the memory 160 and executed by the controller 180.

In the following description, a configuration of the measuring unit 190 for measuring bio-information of a user is explained in detail with reference to FIG. 2.

Figure 2:
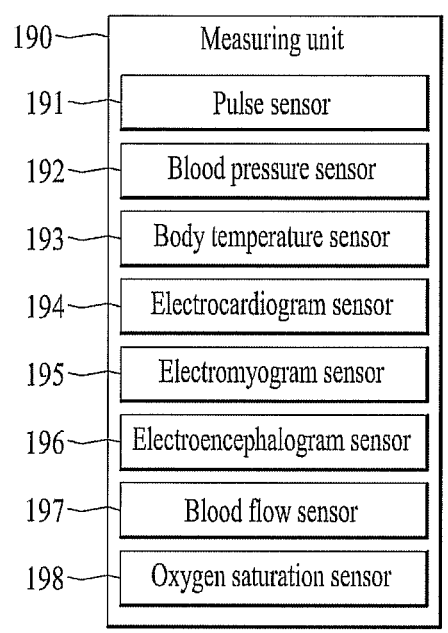
FIG. 2 is a block diagram for a configuration of a measuring unit for measuring bio-information of a user according to the present disclosure.

FIG. 2 is a block diagram for a configuration of a measuring unit for measuring bio-information of a user according to the present disclosure.

Referring to FIG. 2, the measuring unit 190 of the present disclosure measures user's bio-information used for sleep level determination depending on a presence or non-presence of user's sleep and a sleep depth under the control of the controller 180.

In this case, the bio-information of the user may include at least one of a blood pressure, a pulse, a body temperature, an electrocardiogram, an electromyogram, an electroencephalogram, a blood flow, an oxygen saturation and the like.

The above-configured measuring unit 190 may include a pulse sensor 191, a blood pressure sensor 192, a body temperature sensor 193, an electrocardiogram sensor 194, an electromyogram sensor 195, an electroencephalogram sensor 196, a blood flow sensor 197, an oxygen saturation sensor 198 and the like.

In particular, the pulse sensor 191 measures a user's pulse and then outputs the measured pulse to the controller 180. The blood pressure sensor 192 measures a user's blood pressure and then outputs the measured blood pressure to the controller 180.

The body temperature sensor 193 measures a body temperature of a user and then outputs the measured body temperature to the controller 180.

The electrocardiogram sensor 194 measures an electrocardiogram of a user and then outputs the measured electrocardiogram to the controller 180. The electrocardiogram sensor 194 is provided within the terminal 100 or connected to the terminal 100 via the interface unit 170. The electrocardiogram sensor 194 is attached near a heart of a user, measures an electrocardiogram of the user, and then outputs the measured electrocardiogram to the controller 180. Alternatively, the electrocardiogram sensor 194 is configured as an external measurement device and may transmit information corresponding to the measured electrocardiogram of the user to the terminal 100 by a wireless communication such as a short range communication.

The electromyogram sensor 195 measures an electromyogram of a user and then outputs the measured electromyogram to the controller 180. The electromyogram sensor 195 is provided within the terminal 100 or connected to the terminal 100 via the interface unit 170. The electromyogram sensor 195 is attached to at least one body part of the user, measures an electromyogram of the user, and then outputs the measured electromyogram to the controller 180. Alternatively, the electromyogram sensor 195 is configured as an external measurement device and may transmit information corresponding to the measured electromyogram of the user to the terminal 100 by a wireless communication such as a short range communication.

The electroencephalogram sensor 196 measures brain waves of a user according to user's electroencephalogram and then outputs the measured brain waves to the controller 180. The electroencephalogram sensor 196 is provided within the terminal 100 or connected to the terminal 100 via the interface unit 170. The electroencephalogram 196 is attached near a head of a user, measures brain waves of the user, and then outputs the measured brain waves to the controller 180. Alternatively, the electroencephalogram sensor 196 is configured as an external measurement device and may transmit information corresponding to the measured brain waves of the user to the terminal 100 by a wireless communication such as a short range communication.

The blood flow sensor 197 measures a blood flow of a user and then outputs the measured blood flow to the controller 180. The blood flow sensor 197 is provided within the terminal 100 or connected to the terminal 100 via the interface unit 170. The blood flow sensor 197 is attached near a finger of a user, measures a blood flow of the user, and then outputs the measured blood flow to the controller 180. Alternatively, the blood flow sensor 197 is configured as an external measurement device and may transmit information corresponding to the measured blood flow of the user to the terminal 100 by a wireless communication such as a short range communication.

The oxygen saturation sensor 198 measures an oxygen saturation of a user in blood and then outputs the measured oxygen saturation blood flow to the controller 180. The blood oxygen saturation sensor 198 is provided within the terminal 100 or connected to the terminal 100 via the interface unit 170. The oxygen saturation sensor 198 is attached near a finger of a user, measures an oxygen saturation of the user, and then outputs the measured oxygen saturation to the controller 180. Alternatively, the oxygen saturation sensor 198 is configured as an external measurement device and may transmit information corresponding to the measured oxygen saturation of the user to the terminal 100 by a wireless communication such as a short range communication.

Figure 3A:
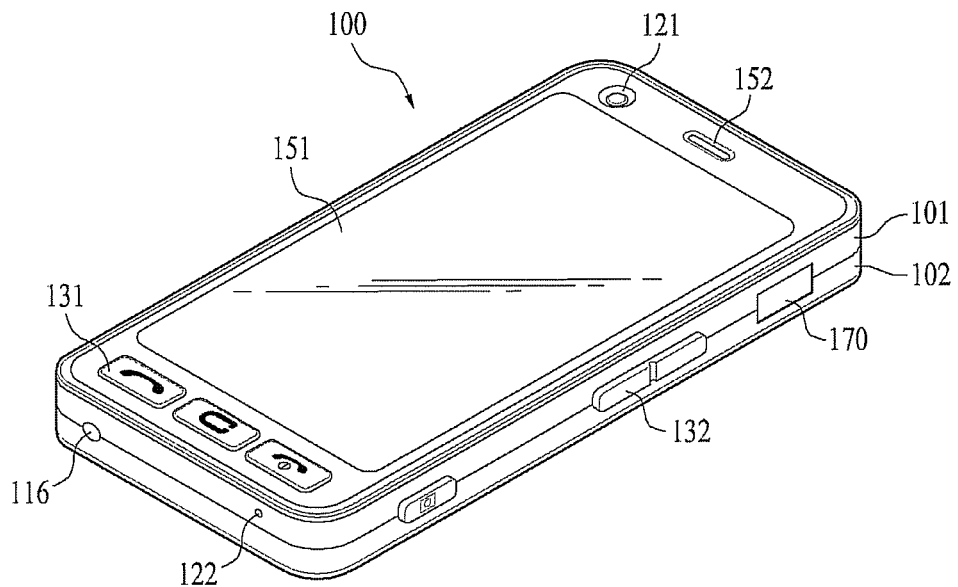
FIG. 3A is a front perspective view of the mobile terminal in accordance with one embodiment of the present disclosure.

FIG. 3A is a front perspective view of the mobile terminal 100 in accordance with one embodiment of the present disclosure. In FIG. 3A, the mobile terminal 100 is shown to have a bar type terminal body.

However, it should be understood that the mobile terminal 100 is not limited to a bar type terminal body and can have various other body types. Examples of such body types include a slide type body, folder type body, swing type body, a rotational type body, or combinations thereof. Although the disclosure herein is primarily with respect to a bar-type mobile terminal 100, it should be understood that the disclosure can be applied to other types of mobile terminals.

As shown in FIG. 3A, the case of the mobile terminal 100 (otherwise referred to as a "casing," "housing," or "cover") forming the exterior of the mobile terminal 100 can include a front case 101 and a rear case 102. Various electronic components are installed in the space between the front case 101 and the rear case 102. One or more intermediate cases can be additionally disposed between the front case 101 and the rear case 102. For example, the front case 101 and the rear case 102 can be made by injection-molding of a synthetic resin or can be made using a metal, such as stainless steel (STS) or titanium (Ti).

The display unit 151, the audio output module 152, the camera 121, user input modules 130a and 130b, the microphone 122, or the interface unit 170 can be situated on the mobile terminal 100, and specifically, on the front case 101.

As shown in FIG. 3A, for example, the display unit 151 can be configured to occupy a substantial portion of the front face 156 of the front case 101. As also shown in FIG. 3A, the audio output unit 152 and the camera 121 can be arranged in proximity to one end of the display unit 151, and the user input module 130a and the microphone 122 can be located in proximity to another end of the display unit 151. As further shown in FIG. 3A, the user input module 130b and the interface unit 170 are arranged on the sides of the front case 101 and the rear case 102, such as sides 158 and 159, respectively.

The user input unit 130 described previously with respect to FIG. 1 can be configured to receive a command for controlling an operation of the mobile terminal 100 and can include one or more user input modules 130a and 130b shown in FIG. 3A. The user input modules 130a and 130b can each be referred to as a "manipulation unit" and can be configured to employ various methods and techniques of tactile manipulation and response to facilitate operation by the user.

The user input modules 130a and 130b can be configured for inputting different commands relative to one another. For example, the user input module 130*a* can be configured allow a user to input such commands as "start," "end," and "scroll" to the mobile terminal 100. The user input module 130*b* can allow a user to input a command for adjusting the volume of the audio output unit 152 or a command for switching to a touch recognition mode of the display unit 151.

Figure 3B:
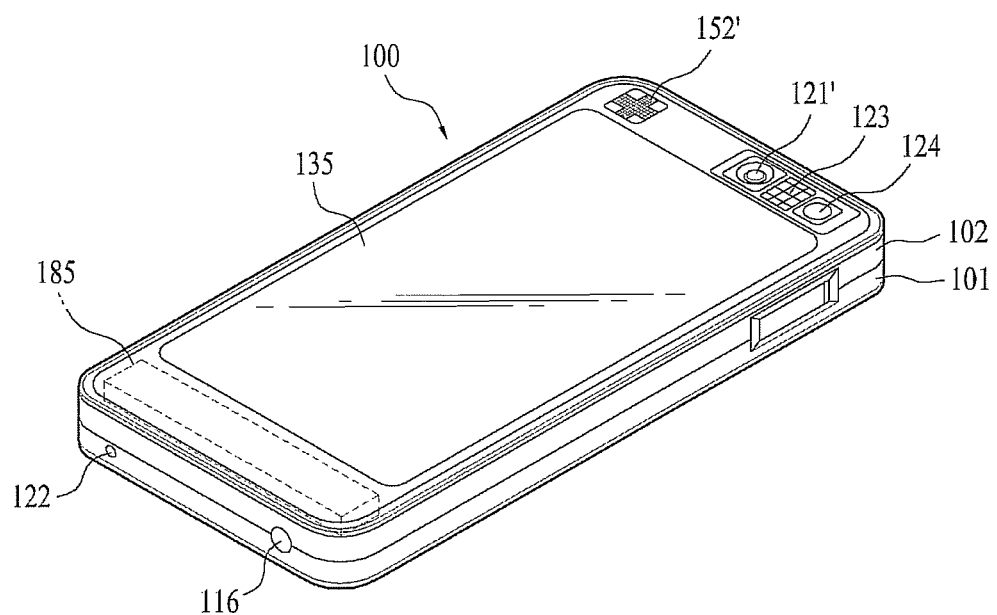
FIG. 3B is a rear perspective view of the mobile terminal in accordance with one embodiment of the present disclosure.

FIG. 3B is a rear perspective view of the mobile terminal 100 in accordance with one embodiment of the present disclosure. As shown in FIG. 3B, a camera 121-1 can be additionally located on a rear surface 161 of the rear case 102. The camera 121-1 has a direction of view that is substantially opposite to the direction of view of the camera 121 shown in FIG. 3A. The cameras 121 and 121-1 can have different resolutions, or different pixels counts, with respect to one another.

For example, the camera 121 can operate with a relatively lower resolution than the camera 121-1 in order to capture an image of the user to allow immediate transmission of the image to another user in real-time for a video call, whereas the camera 121-1 can operate with a relatively higher resolution than the camera 121 to capture images of general objects with high picture quality, which may not require immediate transmission in real-time, and may be stored for later viewing or use. For example, the cameras 121 and the camera 121-1 can be configured to rotate or to pop-up on the mobile terminal 100.

Additional camera related components, such as a flash 123 and a mirror 124, can be located adjacent to the camera 121-1. When an image of a subject is captured with the camera 121-1, the flash 123 illuminates the subject. The mirror 124 allows self-image capturing by allowing the user to see himself when the user desires to capture his own image using the camera 121-1.

The rear surface 161 of the rear case 102 can further include a second audio output module 152-1. The second audio output module 152-1 can support a stereo sound function in conjunction with the audio output module 152 shown in FIG. 3A and can be used for communication during a phone call when the mobile terminal 100 is in a speaker phone mode.

A broadcasting signal receiving antenna 116 can be additionally attached to the side of the body of the mobile terminal 100 in addition to an antenna used for telephone calls. The broadcasting signal receiving antenna 116 can form a part of the broadcast receiving module 111 shown in FIG. 1, and can be set in the body of the mobile terminal 100 such that the broadcasting signal receiving antenna can be pulled out and retracted into the body of the mobile terminal 100.

FIG. 3B shows the power supply unit 190 for providing power to the mobile terminal 100. For example, the power supply unit 190 can be situated either inside the mobile terminal 100 or detachably coupled to the mobile terminal 100.

As shown in FIG. 3B, a touch pad 135 for sensing a touch by the user can be located on the rear surface 161 of the rear case 102. In one embodiment, the touch pad 135 and the display unit 151 can be translucent such that the information displayed on display unit 151 can be output on both sides of the display unit 151 and can be viewed through the touch pad 135. The information displayed on the display unit 151 can be controlled by the touch pad 135. In another embodiment, a second display unit in addition to display unit 151 illustrated in FIG. 3A can be located on the rear surface 161 of the rear case 102 and combined with the touch pad 135 to form a touch screen on the rear case 102.

The touch pad 135 is activated by interconnecting with the display unit 151 of the front case 101. The touch pad 135 can be located in parallel with the display unit 151 and behind the display unit 151. The touch pad 135 can have the same or smaller size than the display unit 151.

Figure 4A:
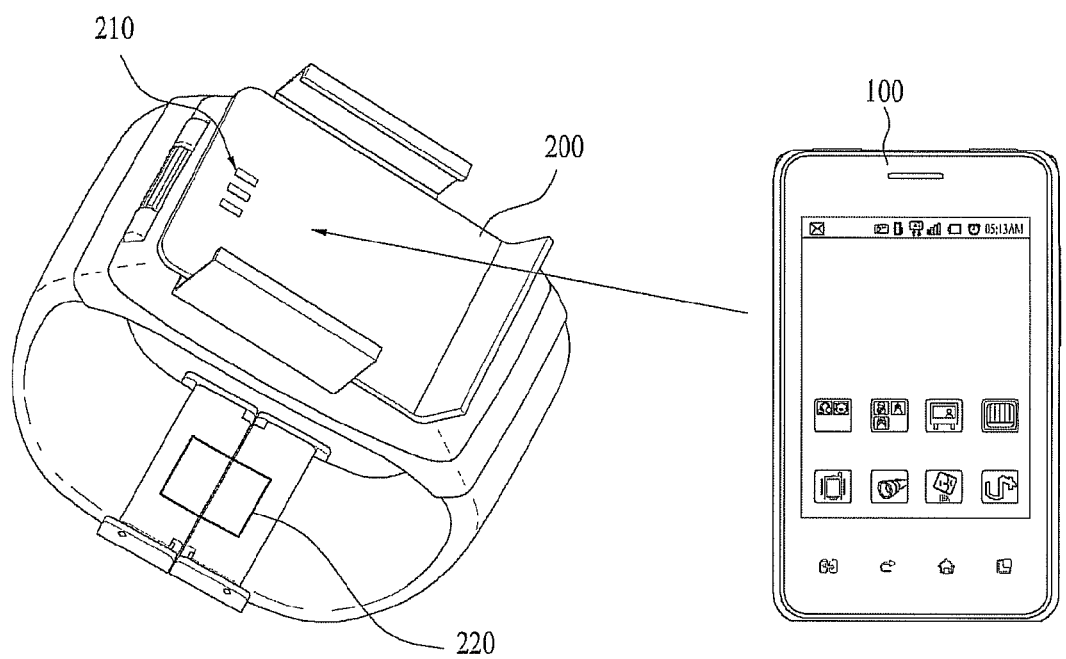
FIGS. 4A and 4B are perspective diagrams of a terminal of a wristwatch type according to the present disclosure.
Figure 4B:
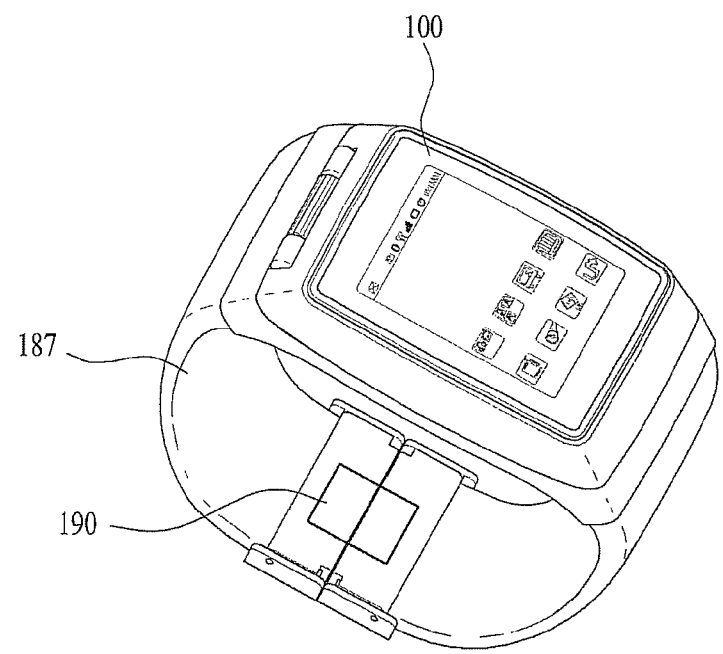

FIGS. 4A and 4B are perspective diagrams of a terminal of a wristwatch type according to the present disclosure.

FIG. 4A shows that a terminal according to the present disclosure includes a mobile terminal 100 and a wristwatch support 200 on which the mobile terminal 100 is detachably mounted. In particular, a user attaches the mobile terminal 100 to the wristwatch support 200, thereby using the mobile terminal 100 as a wristwatch.

In this case, a transceiving unit 210 configured to transceive signals with the mobile terminal 100 is provided to the wristwatch support 200 in a manner of being connected to the interface unit 170 of the mobile terminal 100.

And, the measuring unit 190 described with reference to FIG. 1 and FIG. 2 may be provided not to the mobile terminal 100 but to a surface of the wristwatch support 200 which comes in contact with a body of a user.

For instance, referring to FIG. 4A, a measuring unit 220 (which is the same measuring unit shown in FIG. 1 or FIG. 2) provided to the wristwatch support 200, is formed on the surface which will come in contact with a wrist of a user.

In particular, the measuring unit 220 provided to the wristwatch support 200 can transceive signals with the controller 180 of the mobile terminal 100 via a transceiving unit 210. Under the control of the controller 180, the measuring unit 220 measures bio-information of a user and then outputs the measured bio-information to the controller 180.

FIG. 4B shows that a terminal according to the present disclosure is built in one body with a wristwatch.

Referring to FIG. 4B, the measuring unit 190 is provided to a surface, which comes in contact with a body of a user, of a wrist fixing band 187 of the wrist watch. And, bio-information of a user can be measured through the measuring unit 190.

For clarity of the following description of the present disclosure, assume that a terminal according to the present disclosure is a wristwatch type. Of course, a terminal according to the present disclosure can include one of all terminals of a wearable device type, which is wearable of a user's body, configured to measure bio-information of the user as well as a mobile terminal.

In the following description, a process for providing a snooze function for alarm in accordance with a sleep state of a user after an alarm output according to the present disclosure is explained in detail with reference to FIGS. 5 to 20.

FIG. 5 is a flowchart of a process for providing a snooze function in accordance with a sleep state of a user after an alarm output according to the present disclosure.

Referring to FIG. 5, while an alarm is set in the memory 160 [S110], the controller 180 determines whether a current condition meets an output condition of the alarm [S120].

If the current condition meets the output condition of the alarm [S130], the controller 180 controls the alarm unit 153 to output the set alarm [S140]. In this case, an operation of outputting the alarm may include at least one of an operation of outputting an alarm sound (e.g., audio, vibration sound, a combination of audio and vibration sound, etc.) set for the alarm via the alarm unit 153, an operation of displaying information indicating the alarm on the display unit 151, an operation of blinking a screen of the display unit 151 in specific color to indicate the alarm, and the like.

In this case, the alarm set in the memory 160 may include a general alarm set by a user through an alarm menu of the terminal 100. In particular, the alarm may include an output time of the alarm, an output type (e.g., audio, bell sound, combination of audio and bell sound, etc.) of the alarm, a memo content related to the alarm, and the like. If the alarm is set by a user via the alarm menu, the steps S120 and S130 are skipped. Instead, the alarm is outputted on the alarm time set for the alarm and the steps S150 to S220 described in the following description can be then performed.

Meanwhile, the alarm set in the memory 160 may include an alarm automatically set by the terminal 100 in the memory 160 to prevent a user from falling asleep in a specific situation or awake a user from a sleep (e.g., a short sleep, a long sleep) on a specific condition.

In the following description, a process for automatically setting an alarm by detecting that a user is asleep and a process for outputting the alarm if a current condition meets an output condition of the alarm [i.e., detailed operations of the steps S110 to S140 shown in FIG. 5] are explained in detail with reference to FIGS. 6 to 11.

Figure 6:
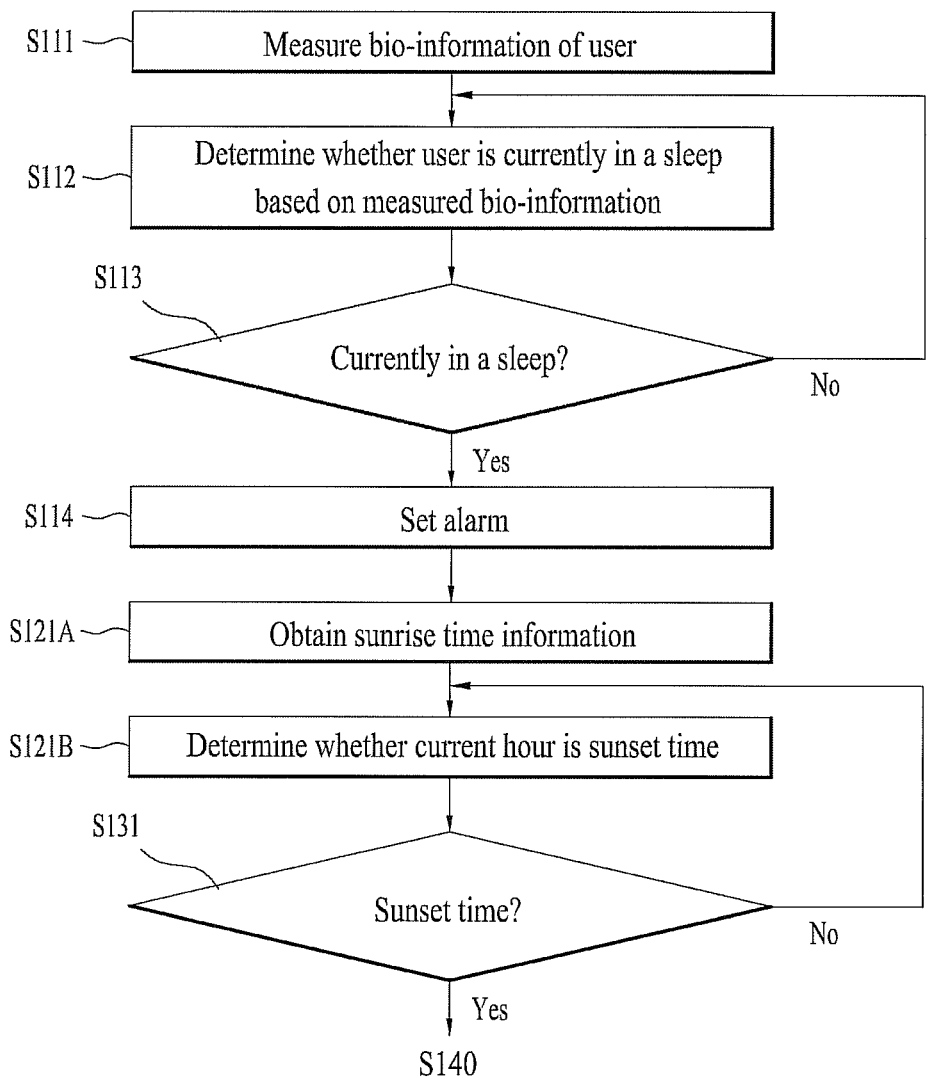
FIG. 6 is a flowchart for detailed operations of the steps S110 to S140 shown in FIG. 5 according to a 1st example of the present disclosure.

FIG. 6 is a flowchart for detailed operations of the steps S110 to S140 shown in FIG. 5 according to a 1st example of the present disclosure.

In particular, FIG. 6 shows a process for automatically outputting an alarm, which was automatically set while a user is asleep, at a sunrise time.

According to FIG. 6, it is not necessary for a user to manipulate a terminal one by one for the alarm setting of the related art. If a user gets a sleep or falls asleep, the terminal 100 automatically sets an alarm when the user starts to get a sleep. And, the alarm is automatically outputted at a sunrise time similar to a morning wakeup time of the user.

Referring to FIG. 6, the controller 180 periodically measures bio-information of a user through the measuring unit 190 [S111]. In this case, as mentioned in the foregoing description with reference to FIG. 2, the bio-information of the user may include at least one or two of a blood pressure, a pulse, a body temperature, an electrocardiogram, an electromyogram, an electroencephalogram, a blood flow, an oxygen saturation and the like.

In this case, as mentioned in the foregoing description with reference to FIG. 2, the measuring unit 190 may be provided within the terminal 100 or as an external measuring device.

If the measuring unit 190 includes the external measuring device, the controller 180 transmits a command signal for periodically measuring the bio-information of the user to the external measuring device via the wireless communication unit 110 and is then able to receive the periodically measured bio-information of the user from the external measuring device via the wireless communication unit 110.

Based on the measured bio-information of the user, the controller 180 determines whether the user starts to fall asleep or is currently asleep.

In particular, the bio-information of the user varies depending on whether the user is in normal activity, starts to fall asleep, or is asleep.

Currently, human sleep stages can be mainly categorized into an REM (rapid eye movement) stage, a 1st non-REM stage, a 2nd non-REM stage, a 3rd non-REM stage and a 4th non-REM stage.

In particular, regarding a human sleep depth, the 1st non-REM stage is deeper than the REM stage, the 2nd non-REM stage is deeper than the 1st non-REM stage, the 3rd non-REM stage is deeper than the 2nd non-REM stage, and the 4th non-REM stage is deeper than the 3rd non-REM stage.

The 1st non-REM stage is the stage corresponding to a start of a doze and includes a period from a non-sleep state to a doze-off state. In the 1st non-REM stage, a surrounding noise is partially recognizable while eyes are slowly moving right and left.

The 2nd non-REM stage is an actually asleep stage and means a relatively light sleep state. In the 2nd non-REM stage, a user wakes up and then realizes that he was asleep.

The 3rd non-REM stage indicates an intermediate sleep state. And, the 4th non-REM stage indicates a deep sleep state.

A human can enter the REM stage through the 1st to 4th non-REM stages.

In the REM stage, eyes are moving fast. The REM stage closer to an awakened state rather than an actually asleep state. In the REM stage, heartbeat, breathing, pulse and blood pressure are increasing. During this stage, a face or hand tends to move frequently.

In particular, if the sleep depth of a person in a sleep corresponds to the REM stage or the 1st non-REM stage, the person just falls asleep or almost wakes up from a sleep. If the sleep depth of a person in a sleep corresponds to one of the 2nd to 3rd non-REM stages, the person has taken a smooth sleep to some extent.

Meanwhile, in the memory 160 of the present disclosure, values of a blood pressure, a pulse, a body temperature, an electrocardiogram, an electromyogram, an electroencephalogram, a blood flow and an oxygen saturation, which correspond to 1st human bio-information in the 1st non-REM stage, values of a blood pressure, a pulse, a body temperature, an electrocardiogram, an electromyogram, an electroencephalogram, a blood flow and an oxygen saturation, which correspond to 2nd human bio-information in the 2nd non-REM stage, values of a blood pressure, a pulse, a body temperature, an electrocardiogram, an electromyogram, an electroencephalogram, a blood flow and an oxygen saturation, which correspond to 3rd human bio-information in the 3rd non-REM stage, values of a blood pressure, a pulse, a body temperature, an electrocardiogram, an electromyogram, an electroencephalogram, a blood flow and an oxygen saturation, which correspond to 4th human bio-information in the 4th non-REM stage, and values of a blood pressure, a pulse, a body temperature, an electrocardiogram, an electromyogram, an electroencephalogram, a blood flow and an oxygen saturation, which correspond to 5th human bio-information in the REM stage, are sorted by sleep stages and then saved as Table 1.

TABLE 1

| Sleep depth | Condition |
| --- | --- |
| $1^{st}$ non-REM stage | $1^{st}$ bio-information |
| $2^{nd}$ non-REM stage | $2^{nd}$ bio-information |
| $3^{rd}$ non-REM stage | $3^{rd}$ bio-information |
| $4^{th}$ non-REM stage | $4^{th}$ bio-information |
| REM stage | $5^{th}$ bio-information |

In particular, the table, in which the 1st to 5th bio-informations on the respective sleep stages are saved, may be saved in the memory 160 by being downloaded from an external device or website via the wireless communication unit 110 or provided as a default to the terminal 100.

Moreover, a user may select at least one or two of a blood pressure, a pulse, a body temperature, an electrocardiogram, an electromyogram, an electroencephalogram, a blood flow and an oxygen saturation, which correspond to the bio-information measurable by the measuring unit 190, through a menu manipulation of the terminal and then controls the selected information to be measured by the measuring unit 190.

For instance, a user selects the pulse, the blood pressure and the body temperature from the blood pressure, the pulse, the body temperature, the electrocardiogram, the electromyogram, the electroencephalogram, the blood flow, and the oxygen saturation through the menu and then enables the selected ones to be measured and used to obtain a presence or non-presence of a sleep of the user and a sleep state of the user.

Based on the user's bio-information measured through the measuring unit 190, the controller 180 can check whether the user currently starts to get a sleep or is in a sleep [S112].

In particular, if the bio-information measured through the measuring unit 190 belongs to the bio-information according to one of the sleep stages of the table saved in the memory 160, the controller 180 can determine that the user currently starts to fall asleep or is asleep.

For instance, since the REM stage or the 1st non-REM stage corresponds to a state in which a sleep depth of a user is lowest, if the bio-information measured through the measuring unit 190 belongs to the 5th bio-information corresponding to the REM stage in Table 1 or the 1st bio-information corresponding to the 1st non-REM stage in Table 1, the controller 180 determines that the user currently starts to get a sleep or is asleep.

Meanwhile, a user can freely select and set the sleep stage, which is used to determine whether the user currently starts to get a sleep or is asleep, from the sleep stages through the menu manipulation. For instance, after the user has set the 2nd non-REM stage through the menu, if the bio-information measured through the measuring unit 190 belongs to the 2nd bio-information according to the user-set 2nd non-REM stage, the controller 180 determines that the user currently starts to get a sleep or is asleep.

As mentioned in the above description, if the controller 180 determines that the user currently starts to get a sleep or is asleep based on the measured bio-information [S113], the controller 180 automatically sets an alarm for awakening the user from the sleep in the memory 160 [S114].

In doing so, an alarm sound of the alarm may be previously set by the user. Alternatively, an alarm sound suitable for an alarm output condition described in the following can be automatically set by the terminal 100.

In particular, in FIG. 6, the alarm output condition set in the memory 160 includes a sunrise time.

After the alarm has been set, the controller 180 accesses a website via the wireless communication unit 110, searches the accessed website for a sunrise time information of the alarm-set date or a sunrise time information of a date next to the alarm-set date and then obtains the found information [S121A].

The controller 180 sets the alarm output time set in the memory 160 to the obtained sunrise time. Moreover, since the alarm output time corresponds to the sunrise time, the controller 180 can automatically set the alarm sound of the alarm to an alarm sound indicating a morning wakeup having a category associated with the sunrise time among alarm sounds provided to the memory 160.

After the alarm setting process has been completed, the controller 180 determines whether a current hour corresponds to the sunrise time of the alarm output condition [S121B]. If the current hour corresponds to the sunrise time [S131], the controller 180 performs the operation corresponding to the step S140.

Figure 7:
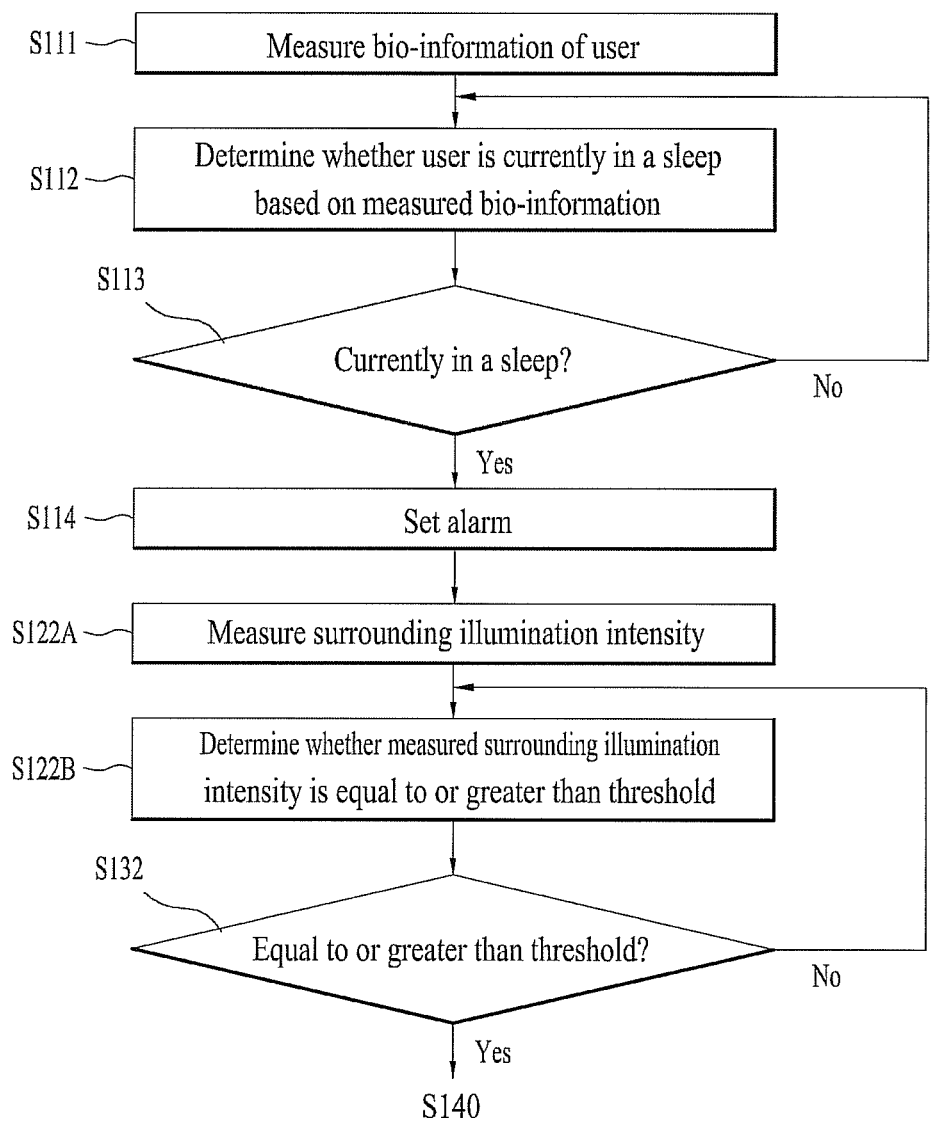
FIG. 7 is a flowchart for detailed operations of the steps S110 to S140 shown in FIG. 5 according to a 2nd example of the present disclosure.

FIG. 7 is a flowchart for detailed operations of the steps S110 to S140 shown in FIG. 5 according to a 2nd example of the present disclosure.

In particular, FIG. 6 shows a process for automatically outputting an alarm, which was automatically set while a user is asleep, if a surrounding illumination intensity is equal to or greater than a threshold.

According to FIG. 7, it is not necessary for a user to manipulate a terminal one by one for the alarm setting of the related art. If a user gets a sleep or falls asleep, the terminal 100 automatically sets an alarm when the user starts to get a sleep. And, the alarm is automatically outputted if the surrounding illumination intensity of the terminal 100 is equal to or greater than an illumination intensity corresponding to a morning.

Since the steps S111 to S114 shown in FIG. 7 are the same as shown in FIG. 6, their details shall be omitted for clarity.

Referring to FIG. 7, if an alarm is set in the memory 160 by the steps S111 to S114, the controller 180 activates the illumination intensity sensor 143, measures a surrounding illumination intensity of the terminal 100 via the illumination intensity sensor 143 [S122A], and then determines whether the measured surrounding illumination intensity is equal to or greater than a threshold [S122B].

In this case, the threshold can become an illumination intensity value corresponding to a normal morning wakeup time. And, a user can freely change the illumination intensity value of the threshold through a menu manipulation suitable for his morning wakeup time.

Since the alarm output condition is associated with a morning illumination intensity value, the controller 180 can set the alarm sound of the alarm to an alarm sound indicating a morning wakeup having a category associated with the morning among alarm sounds provided to the memory 160.

If the measured surrounding illumination intensity is equal to or greater than the threshold [S132], the controller 180 performs an operation corresponding to the step S140 shown in FIG. 5.

Figure 8:
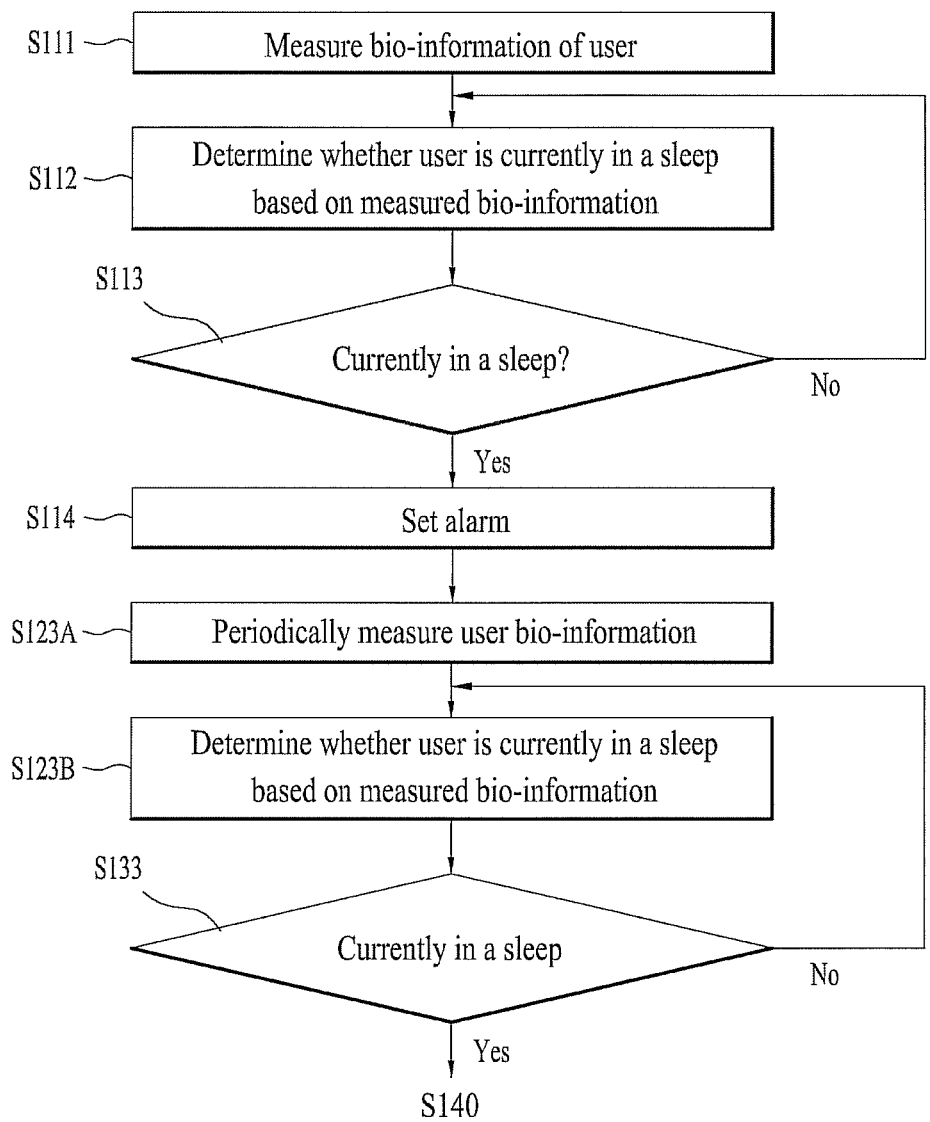
FIG. 8 is a flowchart for detailed operations of the steps S110 to S140 shown in FIG. 5 according to a 3rd example of the present disclosure.

FIG. 8 is a flowchart for detailed operations of the steps S110 to S140 shown in FIG. 5 according to a 3rd example of the present disclosure.

In particular, FIG. 8 shows a process for automatically setting an alarm on an initial doze-off to prevent a doze-off of a user and a process for automatically outputting the alarm if the user dozes off again or keeps dozing off after the alarm setting.

According to FIG. 8, in order to prevent a doze-off, it may be unnecessary for a user to set an alarm, which is to be outputted after a short time, several times. If the user gets a sleep for a short time or dozes off, the terminal 100 automatically detects that the user is dozing off and then automatically sets an alarm. After the alarm has been set, if the user dozes off again or keeps dozing off, the alarm is automatically outputted.

Since the steps S111 to S114 shown in FIG. 8 are the same as shown in FIG. 6, their details shall be omitted for clarity.

Referring to FIG. 8, if an alarm is set in the memory 160 by the steps S111 to S114, the controller 180 controls the measuring unit 190 to periodically measure bio-information of a user again [S123A]. Based on the measured bio-information, the controller 180 determines whether the user dozes off again or whether the user keeps dozing off since a time before the alarm setting [S123B].

In doing so, the user may be unintentionally dozing off. If the user is driving a car, he may be in a dangerous situation. Hence, if the controller 180 determines that the user keeps dozing off, the controller 180 can automatically set the alarm sound of the alarm to a warning sound for awakening the user among the alarm sounds provided to the memory 160.

Meanwhile, as mentioned in the foregoing description with reference to FIG. 6, if the measured bio-information belongs to the 5th bio-information corresponding to the REM stage in Table 1 or the 1st bio-information corresponding to the 1st non-REM stage in Table 1, the controller 180 determines that the user dozes off again or keeps dozing off since a time before the alarm setting [S133] and then performs the operation corresponding to the step S140 shown in FIG. 5.

Figure 9:
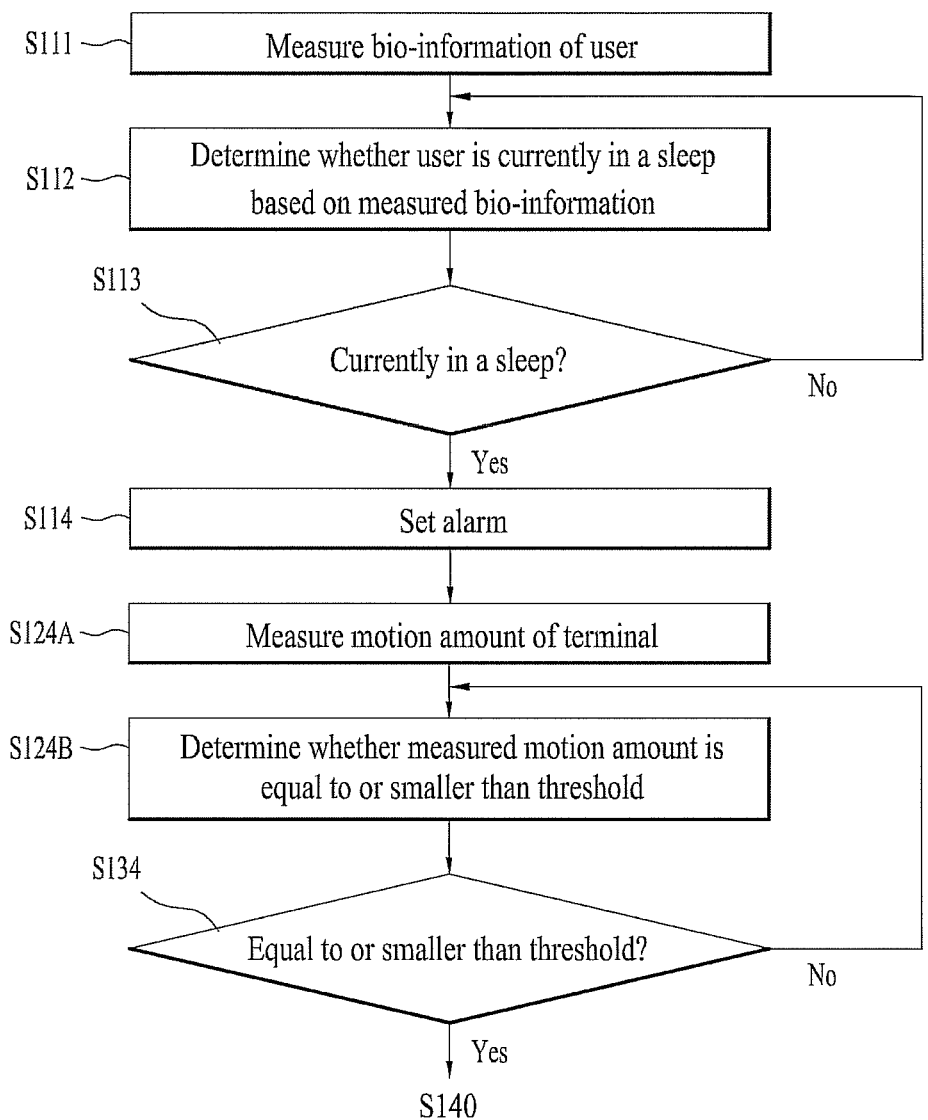
FIG. 9 is a flowchart for detailed operations of the steps S110 to S140 shown in FIG. 5 according to a 4th example of the present disclosure.

FIG. 9 is a flowchart for detailed operations of the steps S110 to S140 shown in FIG. 5 according to a 4th example of the present disclosure.

In particular, FIG. 9 shows a process for automatically setting an alarm in case of an initial doze-off in order to prevent a user's doze-off and a process for automatically outputting the alarm in case of an almost non-presence of a motion of a user wearing a terminal after the alarm setting.

According to FIG. 9, in order to prevent a user's doze-off, it may be unnecessary for a user to set an alarm, which is to be outputted after a short time, several times. The terminal 100 automatically detects that the user is dozing off and then automatically sets an alarm. After the alarm has been set, as the user dozes off, if there is almost no motion, the alarm is automatically outputted.

Since the steps S111 to S114 shown in FIG. 9 are the same as shown in FIG. 6, their details shall be omitted for clarity.

Referring to FIG. 9, if an alarm is set in the memory 160 by the steps S111 to S114, the controller 180 activates the motion sensor 142, measures a motion amount of the terminal 100 caused by a user through the motion sensor 142 [S124A], and then determines whether the measured motion amount is equal to or smaller than a threshold [S124B].

In this case, the threshold may include a normal motion amount of the terminal 100 corresponding to a case that the user wearing the terminal 100 is sleeping or dozing off. And, the user can freely change a desired motion amount of the threshold through a menu manipulation.

In doing so, the user may be unintentionally dozing off. If the user is driving a car, he may be in a dangerous situation. Hence, if the controller 180 determines that the user keeps dozing off, the controller 180 can automatically set the alarm sound of the alarm to a warning sound for awakening the user among the alarm sounds provided to the memory 160.

If the measured motion amount is equal to or smaller than the threshold [S124B], the controller 180 determines that the user dozes off or keeps dozing off since a time before the alarm setting and then performs the operation corresponding to the step S140 shown in FIG. 5.

Figure 10:
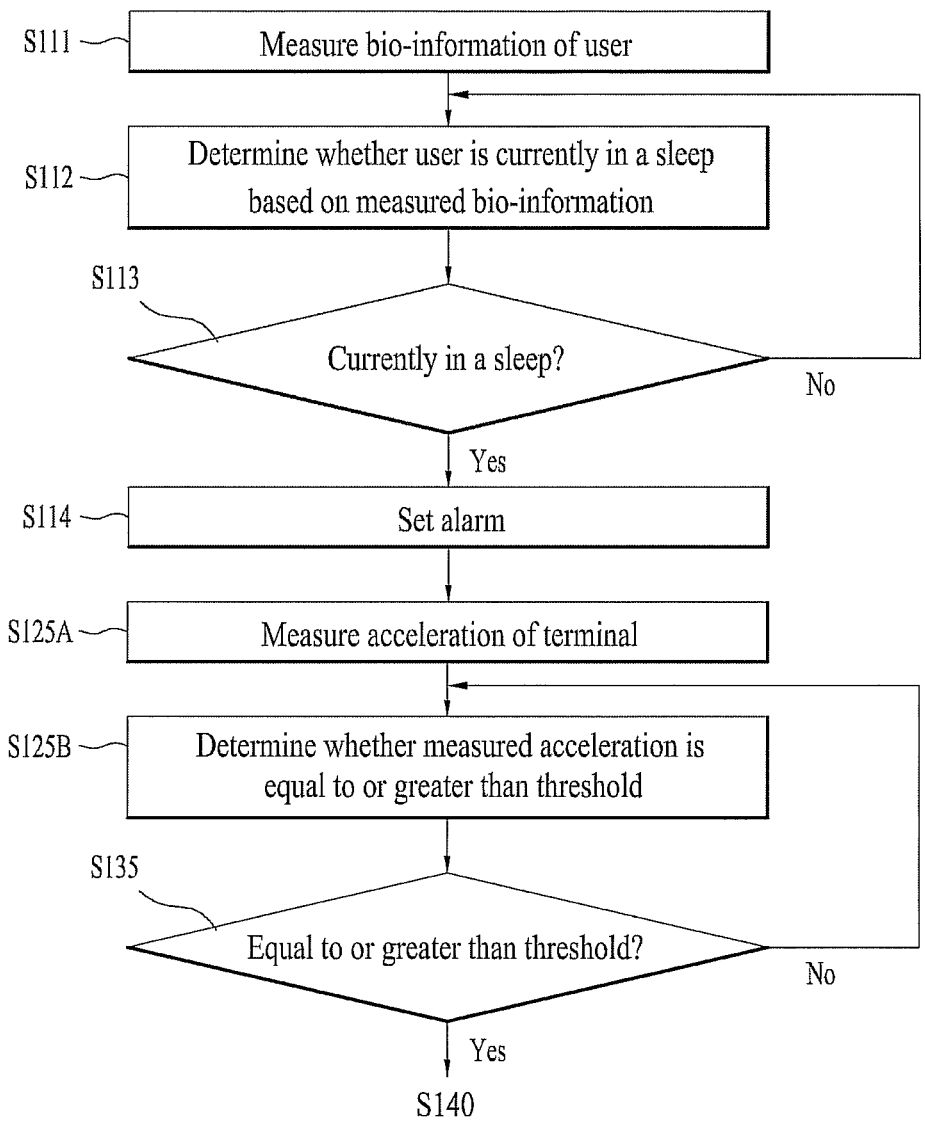
FIG. 10 is a flowchart for detailed operations of the steps S110 to S140 shown in FIG. 5 according to a 5th example of the present disclosure.

FIG. 10 is a flowchart for detailed operations of the steps S110 to S140 shown in FIG. 5 according to a 5th example of the present disclosure.

In particular, FIG. 10 shows a process for automatically setting an alarm in case of an initial doze-off of a user in order to prevent a user's doze-off at the wheel and a process for automatically outputting the alarm in case that an acceleration measured in the terminal after the alarm setting is equal to or greater than a threshold.

According to FIG. 10, it is able to use an alarm to awaken a currently dozing user at the wheel in response to a driving speed.

Since the steps S111 to S114 shown in FIG. 10 are the same as shown in FIG. 6, their details shall be omitted for clarity.

Referring to FIG. 10, if an alarm is set in the memory 160 by the steps S111 to S114, the controller 180 activates the acceleration sensor 144, measures an acceleration (or deceleration) of the terminal 100 through the acceleration sensor 144 [S125A], and then determines whether the measured acceleration is equal to or greater than a threshold [S125B].

In this case, the threshold may include an acceleration enough to actually move a vehicle (e.g., a bicycle, a bike, a car, etc.) by a driving of a user who has started to drive the vehicle by wearing the terminal 100. And, the user can freely change a desired acceleration value through a menu manipulation.

In doing so, the user may be dozing off. If the user is driving a car, he may be in a dangerous situation. Hence, if the controller 180 determines that the user keeps dozing off at the wheel, the controller 180 can automatically set the alarm sound of the alarm to a warning sound for awakening the user among the alarm sounds provided to the memory 160.

If the measured acceleration is equal to or greater than the threshold [S135], the controller 180 determines that the user is asleep or keeps dozing off at the wheel and then performs the operation corresponding to the step S140 shown in FIG. 5.

Figure 11:
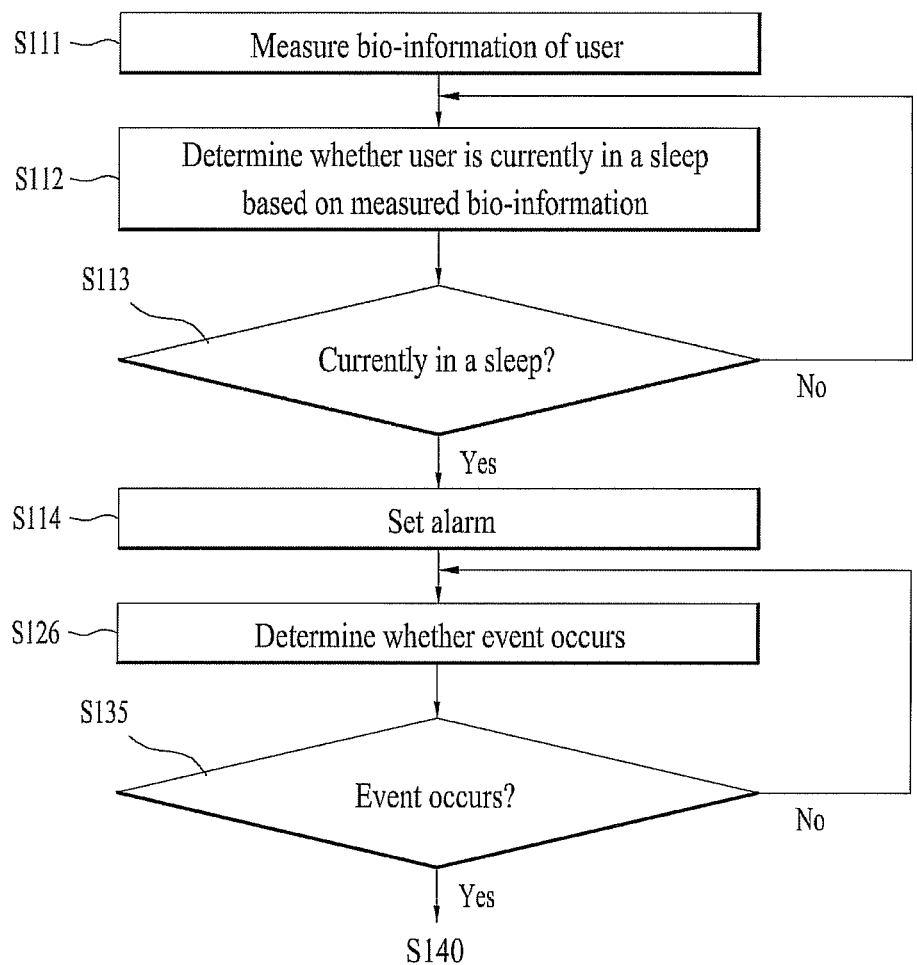
FIG. 11 is a flowchart for detailed operations of the steps S110 to S140 shown in FIG. 5 according to a 7th example of the present disclosure.

FIG. 11 is a flowchart for detailed operations of the steps S110 to S140 shown in FIG. 5 according to a 7th example of the present disclosure.

In particular, while a user is asleep, after an alarm has been automatically set, FIG. 11 shows a process for automatically outputting an alarm in case of an occurrence of a specific event.

According to FIG. 11, while a user is dozing off, if at least one event (e.g., a call reception, an SMS/MMS message reception, an email reception, an instant message reception, a reserved broadcast viewing time indication, a schedule indication, etc.) occurs, the alarm is automatically outputted in order to prevent the user from being unable to recognize the event occurrence.

Since the steps S111 to S114 shown in FIG. 11 are the same as shown in FIG. 6, their details shall be omitted for clarity.

Referring to FIG. 11, after an alarm has been set in the memory 160 by the steps S111 to S114, the controller 180 determines whether a specific event occurs in the terminal 100 [S126].

In this case, the specific event may include at least one of a call reception, an SMS/MMS message reception, an email reception, an instant message reception, a schedule indication and the like. And, the user can freely set at least one event to receive an indication of the event occurrence through the alarm among the types of the events through a menu manipulation.

After the alarm has been set, if the specific event occurs [S136], the controller 180 performs the operation corresponding to the step S140 shown in FIG. 5 to inform the user of the occurrence of the specific event.

So far, the detailed operations of the steps S110 to S140 are described in detail with reference to FIGS. 6 to 11.

Referring now to FIG. 5, after the alarm has been outputted, the controller 180 controls the measuring unit 190 to measure the bio-information of the user [S150] and then determines whether the user is currently asleep based on the bio-information [S160].

The user bio-information measuring step performed by the measuring unit 190 and the step of determining whether the user is currently asleep based on the bio-information are already described in detail with reference to FIG. 6.

If the controller 180 determines that the user is currently asleep based on the bio-information [S170], the controller 180 starts a snooze function for the alarm [S180].

Moreover, if the user is not currently asleep based on the bio-information, the controller 180 completely ends the alarm [S190].

Once the snooze function is started, the controller 180 controls the measuring unit 190 to measure the bio-information of the user [S200] and then checks a sleep state according to a user's sleep depth based on the measured bio-information of the user [S210].

In particular, as mentioned in the foregoing description with reference to FIG. 6 and Table 1, the controller 180 periodically measures the bio-information of the user and then periodically checks that the user's sleep state belongs to which one of the REM stage and the 1st to 4th non-REM stages.

Thereafter, based on the checked or obtained sleep state of the user, the controller 180 determines whether to end the snooze function [S220].

Meanwhile, referring to FIGS. 12A to 12C and FIG. 13 shown in the following, before the snooze functions is started or after the snooze function has been started, a user can set or change at least one of a snooze repetitive period, snooze repetitive count and alarm sound of the snooze function.

Figure 12A:
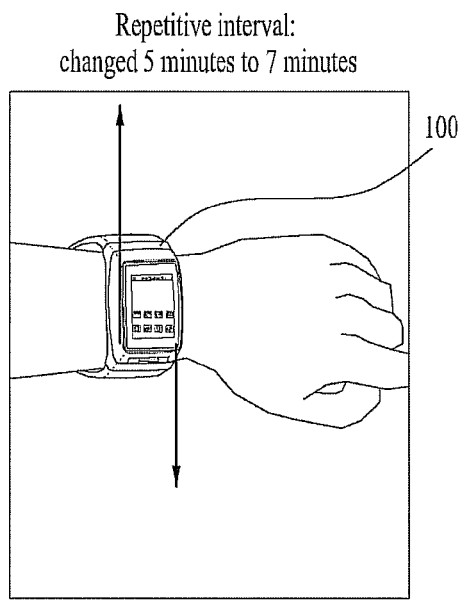
FIGS. 12A to 12C are diagrams to describe a process for setting or changing at least one of a snooze repetitive period, a snooze repetitive count and an alarm sound of a snooze function using a motion gesture.
Figure 12B:
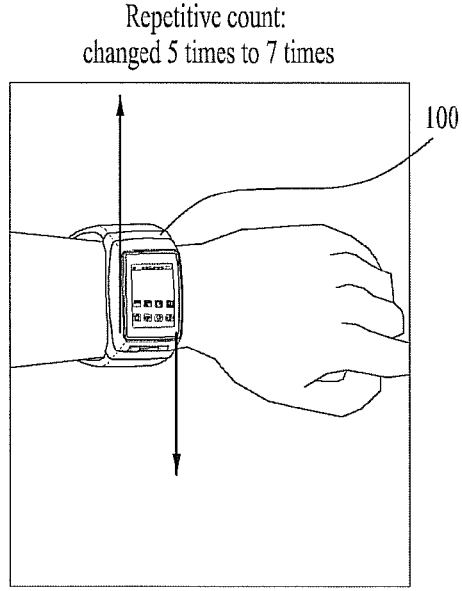
Figure 12C:
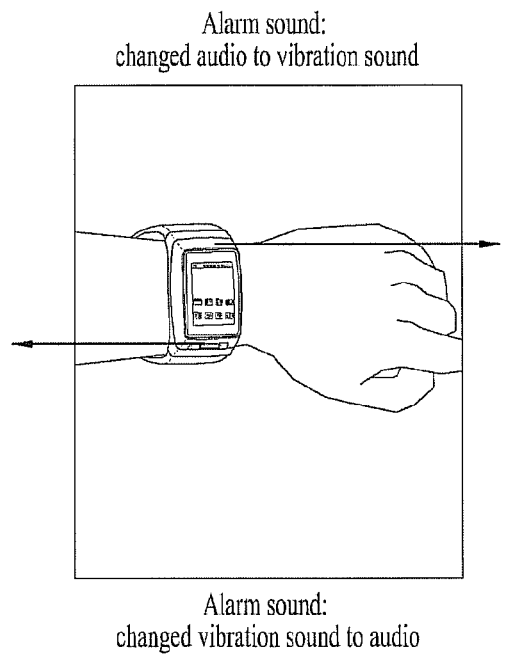

FIGS. 12A to 12C are diagrams to describe a process for setting or changing at least one of a snooze repetitive period, a snooze repetitive count and an alarm sound of a snooze function using a motion gesture.

According to FIGS. 12A to 12C, a user inputs a motion gesture to the terminal 100, thereby changing at least one of a snooze repetitive period, a snooze repetitive count and an alarm sound of a snooze function.

Referring to FIG. 12A, before or after activation of the snooze function, if a user's motion gesture is inputted via the motion sensor 142, the controller 180 can change a snooze repetitive period of the snooze function in response to the inputted motion gesture.

For instance, if an upward motion gesture is inputted, the controller 180 can change a current repetitive period '5 minutes' of the snooze function into '7 minutes'. For another instance, if a downward motion gesture opposed to the upward motion gesture is inputted, the controller 180 can change a current repetitive period '5 minutes' of the snooze function into '3 minutes'. For another instance, if a left motion gesture is inputted in a left direction, the controller 180 can change a current repetitive period '5 minutes' of the snooze function into '7 minutes'. For further instance, if a right motion gesture opposed to the left motion gesture is inputted, the controller 180 can change a current repetitive period '5 minutes' of the snooze function into '3 minutes'.

Referring to FIG. 12B, before or after activation of the snooze function, if a user's motion gesture is inputted via the motion sensor 142, the controller 180 can change a snooze repetitive count of the snooze function in response to the inputted motion gesture.

For instance, if an upward motion gesture is inputted, the controller 180 can change a current repetitive count '5 times' of the snooze function into '7 times'. For another instance, if a downward motion gesture opposed to the upward motion gesture is inputted, the controller 180 can change a current repetitive count '5 times' of the snooze function into '3 times'. For another instance, if a left motion gesture is inputted in a left direction, the controller 180 can change a current repetitive count '5 times' of the snooze function into '7 times'. For further instance, if a right motion gesture opposed to the left motion gesture is inputted, the controller 180 can change a current repetitive count '5 times' of the snooze function into '3 times'.

Referring to FIG. 12C, before or after activation of the snooze function, if a user's motion gesture is inputted via the motion sensor 142, the controller 180 can change an alarm sound of the snooze function in response to the inputted motion gesture.

For instance, if an upward motion gesture is inputted, the controller 180 can change a current alarm sound 'audio' of the snooze function into 'vibration sound'. For another instance, if a downward motion gesture opposed to the upward motion gesture is inputted, the controller 180 can toggle a current alarm sound 'vibration sound' of the snooze function into 'alarm sound'.

Figure 13A:
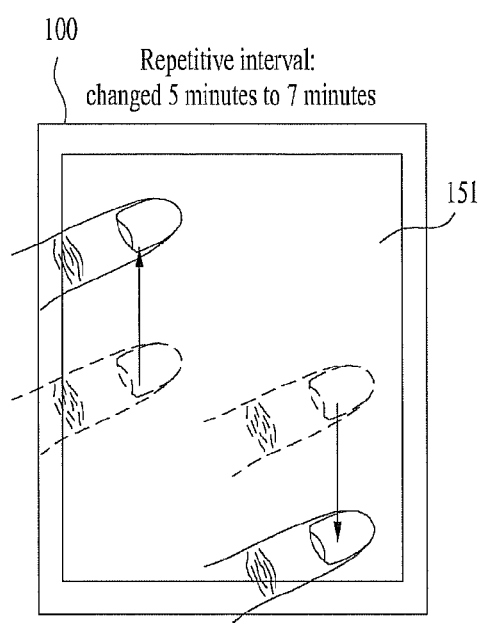
FIGS. 13A to 13C are diagrams to describe a process for setting or changing at least one of a snooze repetitive period, a snooze repetitive count and an alarm sound of a snooze function using a touch gesture.
Figure 13B:
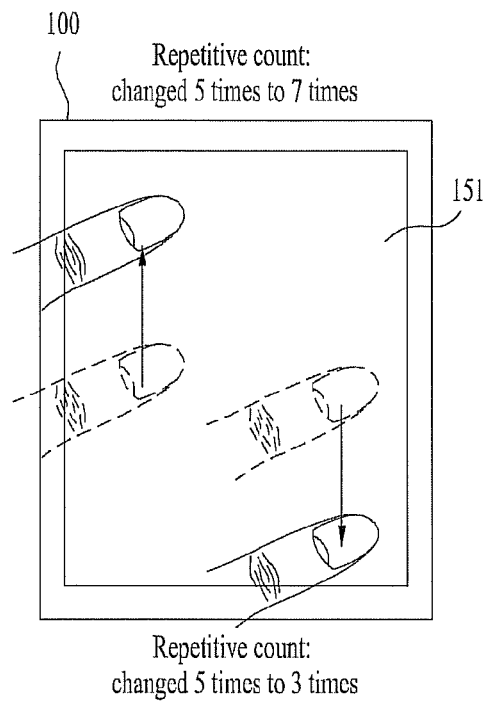
Figure 13C:
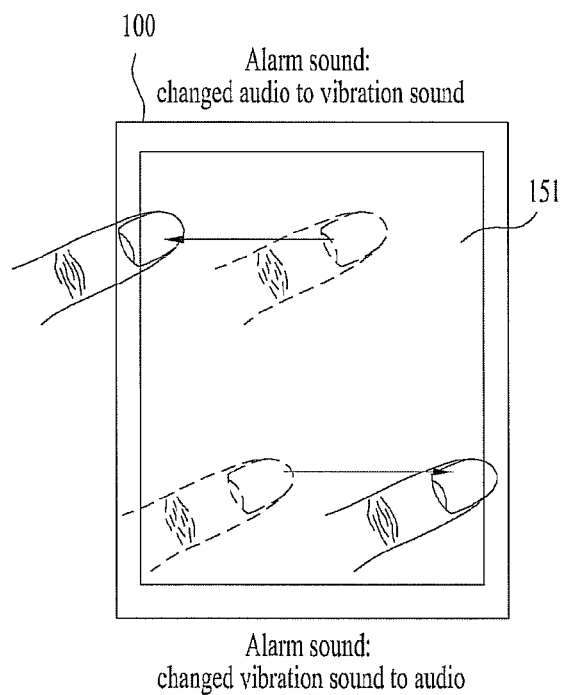

FIGS. 13A to 13C are diagrams to describe a process for setting or changing at least one of a snooze repetitive period, a snooze repetitive count and an alarm sound of a snooze function using a touch gesture.

Referring to FIG. 13A, before or after activation of the snooze function, if a user's touch gesture is inputted to the touchscreen 151, the controller 180 can change a snooze repetitive period of the snooze function in response to the inputted touch gesture.

For instance, if a touch gesture dragged in top direction is inputted, the controller 180 can change a current repetitive period '5 minutes' of the snooze function into '7 minutes'. For another instance, if a touch gesture dragged in bottom direction opposed to the top direction is inputted, the controller 180 can change a current repetitive period '5 minutes' of the snooze function into '3 minutes'. For another instance, if a touch gesture dragged in left direction is inputted, the controller 180 can change a current repetitive period '5 minutes' of the snooze function into '7 minutes'. For further instance, if a touch gesture dragged in right direction opposed to the left direction is inputted, the controller 180 can change a current repetitive period '5 minutes' of the snooze function into '3 minutes'.

Referring to FIG. 13B, before or after activation of the snooze function, if a user's touch gesture is inputted to the touchscreen 151, the controller 180 can change a snooze repetitive count of the snooze function in response to the inputted touch gesture.

For instance, if a touch gesture dragged in top direction is inputted, the controller 180 can change a current repetitive count '5 times' of the snooze function into '7 times'. For another instance, if a touch gesture dragged in bottom direction opposed to the top direction is inputted, the controller 180 can change a current repetitive count '5 times' of the snooze function into '3 times'. For another instance, if a touch gesture dragged in left direction is inputted, the controller 180 can change a current repetitive count '5 times' of the snooze function into '7 times'. For further instance, if a touch gesture dragged in right direction opposed to the left direction is inputted, the controller 180 can change a current repetitive count '5 times' of the snooze function into '3 times'.

Referring to FIG. 13C, before or after activation of the snooze function, if a user's touch gesture is inputted via the touch sensor 142, the controller 180 can change an alarm sound of the snooze function in response to the inputted touch gesture.

For instance, if a touch gesture dragged in left direction is inputted, the controller 180 can change a current alarm sound 'audio' of the snooze function into 'vibration sound'. For another instance, if a touch gesture dragged in right direction opposed to the left direction is inputted, the controller 180 can toggle a current alarm sound 'vibration sound' of the snooze function into 'alarm sound'.

In the following description, the steps S210 and S220 shown in FIG. 5 are explained in detail with reference to FIG. 14.

Figure 14:
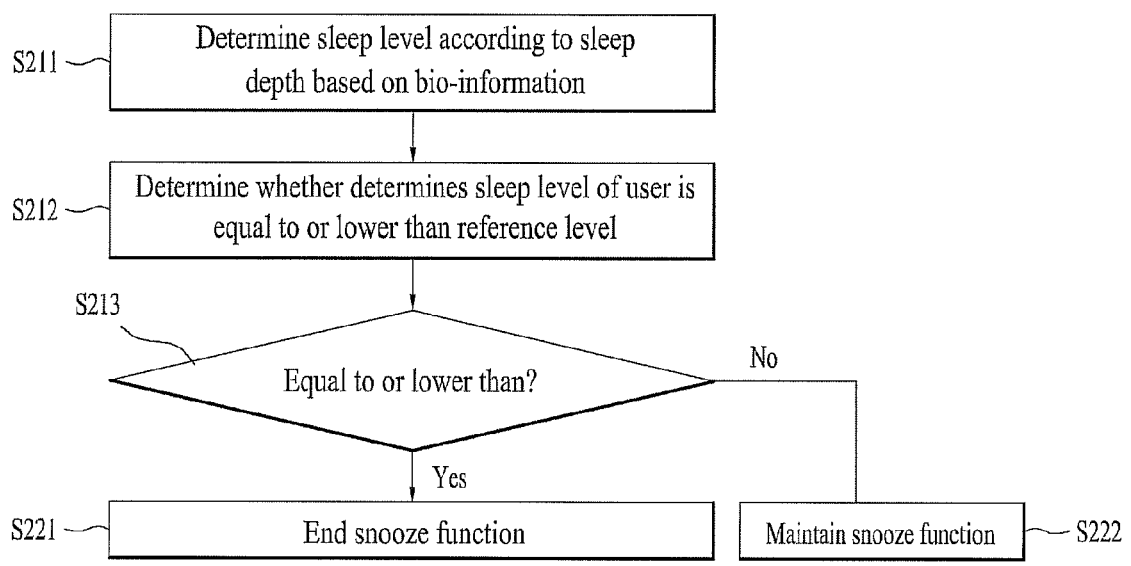
FIG. 14 is a flowchart for detailed operations of the steps S210 and S220 shown in FIG. 5.

FIG. 14 is a flowchart for detailed operations of the steps S210 and S220 shown in FIG. 5.

Referring to FIG. 14, the controller 180 determines a sleep level in accordance with a sleep depth of a user based on the user's bio-information measured by the measuring unit 190 [S211].

In this case, the sleep level may be determined as one of the REM stage and the 1st to 4th non-REM stages described with reference to Table 1.

Subsequently, the controller 180 determines whether the determined sleep level is equal to or lower than a reference level [S212].

In this case, the reference level is a shallow depth of the user's sleep depth and may include one of the REM stage and the 1st to 4th non-REM stages for example. Of course, a user can freely set one of the REM stage and the 1st to 4th non-REM stages to use as the reference level through a menu manipulation.

If the determined sleep level is equal to or lower than the reference level [S213], since the user's sleep state corresponds to a state in which the user is in a light sleep enough not to be awakened by recognizing a snooze function for a current alarm, the controller 180 ends the snooze function [S221].

On the contrary, if the determined sleep level is not equal to or lower than the reference level, since the user's sleep state corresponds to a state in which the user is in a deep sleep enough not to recognize a snooze function for a current alarm, the controller 180 keeps the snooze function [S222].

Figure 15:
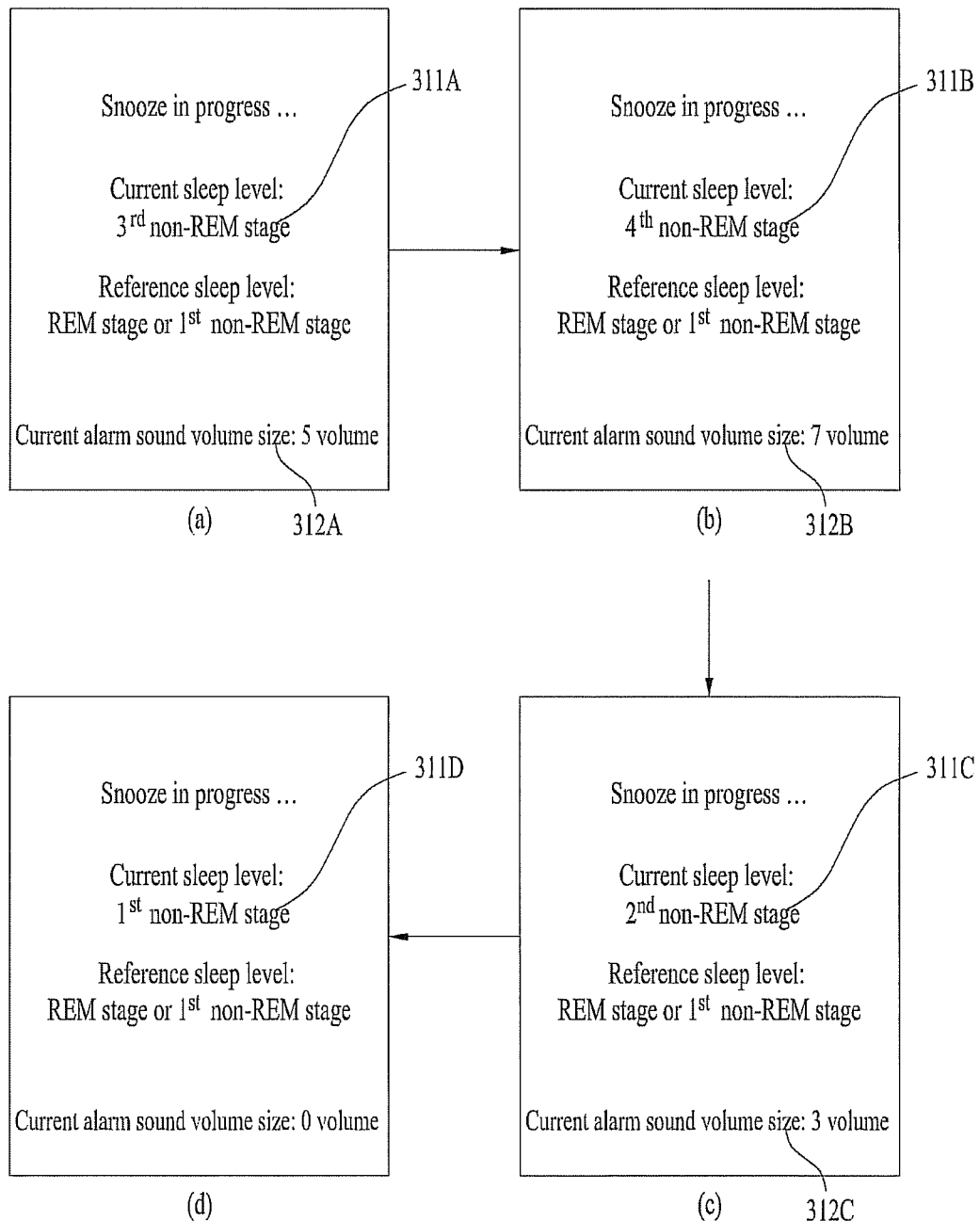
FIG. 15 is a diagram to describe a process for changing an alarm sound output strength of a snooze function in response to a difference between a user's sleep level and a reference level according to the present disclosure.

Meanwhile, once the sleep level according to the user's sleep depth is determined, referring to FIG. 15, the controller 180 can change an output strength of an alarm sound of the snooze function depending on a difference between the determined sleep level and the reference level.

FIG. 15 is a diagram to describe a process for changing an alarm sound output strength of a snooze function in response to a difference between a user's sleep level and a reference level according to the present disclosure.

Referring to FIG. 15, if the determined sleep level of the user gets closer to the reference level, the controller 180 can control a volume of the alarm sound of the snooze function to become gradually lower. On the contrary, if the determined sleep level of the user gets more distant from the reference level, the controller 180 can control a volume of the alarm sound of the snooze function to become gradually higher.

In particular, if the determined sleep level of the user gets gradually closer to the reference level, the sleep state of the user changes into a light sleep from which the user can wake up with ease, which enables a currently outputted alarm sound of the snooze function to be easily recognizable. Therefore, the volume size of the alarm sound of the snooze function is gradually lowered.

On the contrary, if the determined sleep level of the user gets more distant from the reference level gradually, the sleep state of the user changes into a deep sleep from which the user is unable to wake up with ease, which enables a currently outputted alarm sound of the snooze function not to be easily recognizable. Therefore, the volume size of the alarm sound of the snooze function is gradually raised.

For instance, when a volume size of a currently outputted alarm sound of a snooze function is '5' 312A and a currently determined sleep level of a user is '3rd non-REM stage' 311A [FIG. 15 (*a*)], if the sleep level of the user is changed from the '3rd non-REM stage' 311A into '4th non-REM stage' 311B based on user's bio-information periodically measured by the measuring unit 190 [FIG. 15 (*b*)], the sleep level becomes distant from the reference level. Therefore, the controller 180 changes the volume size '5' 312A of the alarm sound in the '3rd non-REM stage' 311A into '7' 312B [FIG. 15 (*b*)].

Referring to FIG. 15 (*c*), if the sleep level of the user is changed from the '4th non-REM stage' 311B into '2nd non-REM stage' 311C based on user's bio-information periodically measured by the measuring unit 190, the sleep level becomes close to the reference level. Therefore, the controller 180 changes the volume size '7' 312B of the alarm sound in the '4th non-REM stage' 311B into '3' 312C.

Referring to FIG. 15 (*d*), if the sleep level of the user is changed from the '2nd non-REM stage' 311C into '1st non-REM stage' 311D based on user's bio-information periodically measured by the measuring unit 190, the sleep level becomes equal to or lower than the reference level. Therefore, the controller 180 ends the snooze function.

Figure 16:
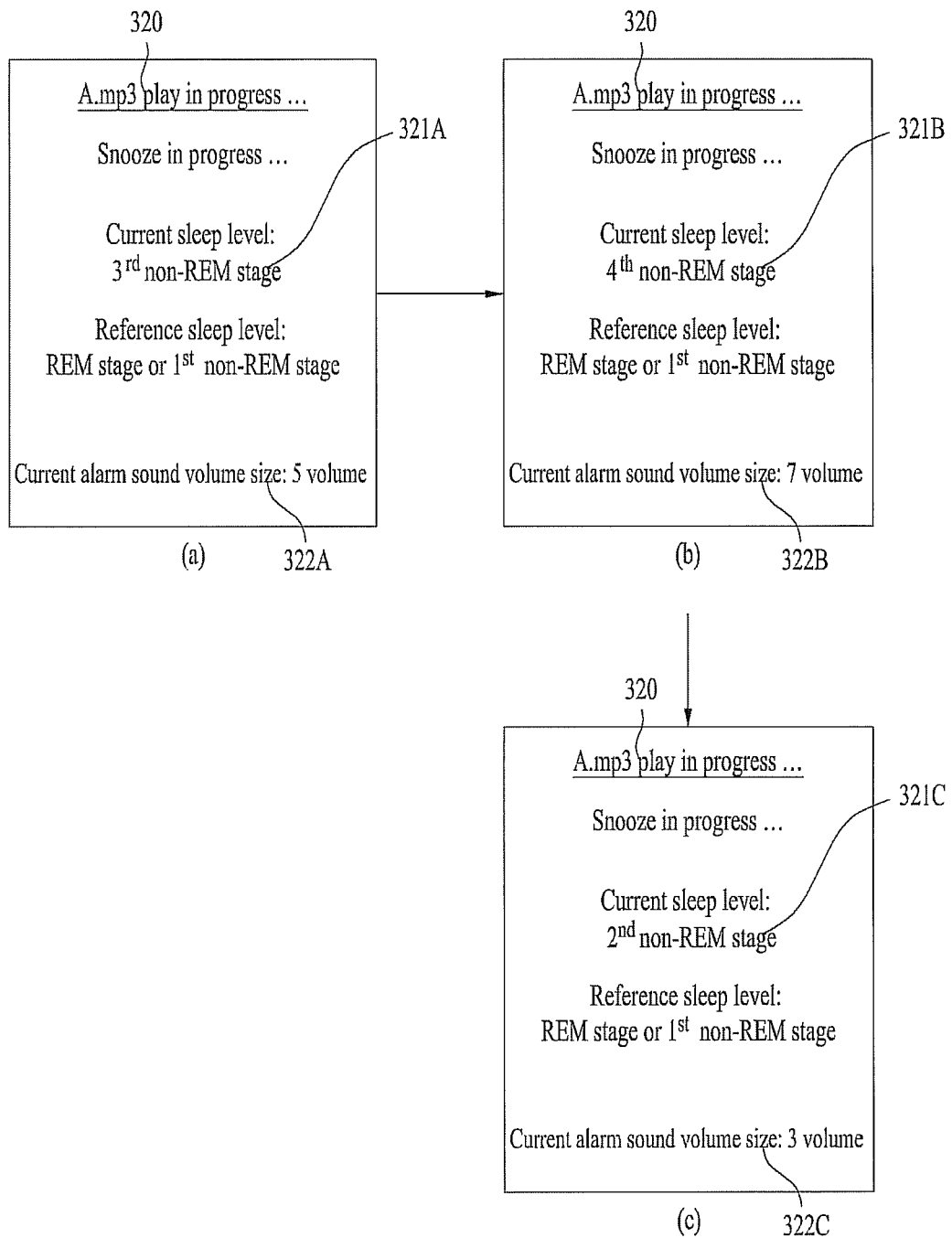
FIG. 16 is a diagram to describe a process for changing a volume size of a sound of a currently played content in response to a difference between a user's sleep level and a reference level according to a 1st example of the present disclosure.

Meanwhile, while a content containing a specific audio is played, if the snooze function is activated like the step S180 shown in FIG. 5 and the sleep level according to the user's sleep depth is determined like the step S211 shown in FIG. 14, referring to FIG. 16, the controller 180 can change a volume size of the audio of the currently played content in response to a difference between the determined sleep level and the reference level.

FIG. 16 is a diagram to describe a process for changing a volume size of a sound of a currently played content in response to a difference between a user's sleep level and a reference level according to a 1st example of the present disclosure.

Referring to FIG. 16, while a content containing a specific audio is played, the snooze function is activated and the sleep level of the user is determined. In doing so, if the determined sleep level of the user gets closer to the reference level, the controller 180 can control a volume size of an audio of the currently played content to become gradually lower. On the contrary, if the determined sleep level of the user gets more distant from the reference level, the controller 180 can control a volume size of the audio of the currently played content to become gradually higher.

In this case, the content may include all kinds of playable multimedia data containing audio.

In particular, a user can get a sleep while listening to music. In doing so, referring to FIG. 16, the user can be led to wake up quickly through a size of a volume of the music instead of the alarm sound of the snooze function. Alternatively, the user can be led to wake up quickly using a size of a volume of the music in addition to the alarm sound of the snooze function.

If the determined sleep level of the user gets gradually closer to the reference level, the sleep state of the user gradually changes into a light sleep from which the user can wake up with ease, which enables a currently outputted audio of the content to be easily recognizable. Therefore, the volume size of the audio of the content is gradually lowered.

On the contrary, if the determined sleep level of the user gets more distant from the reference level gradually, the sleep state of the user gradually changes into a deep sleep from which the user is unable to wake up with ease, which enables a currently outputted audio of the content not to be easily recognizable. Therefore, the volume size of the audio of the content is gradually raised.

For instance, when a volume size of an audio of a currently played content 320 is '5' 322A and a currently determined sleep level of a user is '3rd non-REM stage' 321A [FIG. 16 (*a*)], if the sleep level of the user is changed from the '3rd non-REM stage' 321A into '4th non-REM stage' 321B based on user's bio-information periodically measured by the measuring unit 190 [FIG. 16 (*b*)], the sleep level becomes distant from the reference level. Therefore, the controller 180 raises the volume size '5' 322A of the audio of the content 320 in the '3rd non-REM stage' 321A into '7' 322B [FIG. 16 (*b*)].

Referring to FIG. 16 (*c*), if the sleep level of the user is changed from the '4th non-REM stage' 321B into '2nd non-REM stage' 321C based on user's bio-information periodically measured by the measuring unit 190, the sleep level becomes close to the reference level. Therefore, the controller 180 lowers the volume size '7' 322B of the audio of the content 320 in the '4th non-REM stage' 321B to '3' 322C.

While a content containing a specific audio is played, the snooze function is activated like the step S180 shown in FIG. 5 and the sleep level according to the user's sleep depth is determined like the step S211 shown in FIG. 14. In doing so, referring to FIG. 17, if the determined sleep level is equal to or lower than the reference level, the controller 180 can end the snooze function and lower the audio volume of the content. If the determined sleep level is higher than the reference level, the controller 180 can stop the audio output of the content or end the playback of the content completely.

Figure 17:
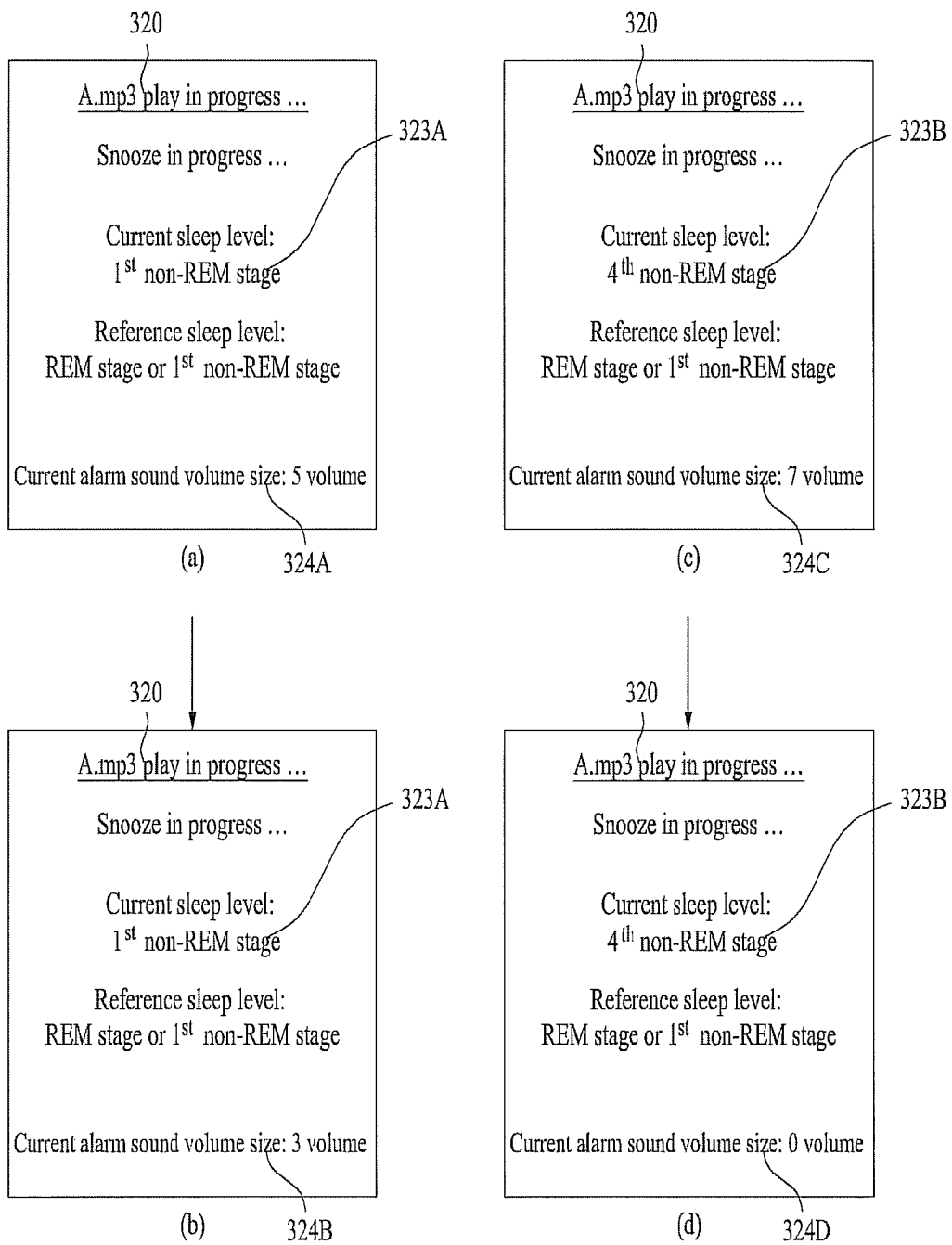
FIG. 17 is a diagram to describe a process for changing a volume size of a sound of a currently played content in response to a difference between a user's sleep level and a reference level according to a 2nd example of the present disclosure.

FIG. 17 is a diagram to describe a process for changing a volume size of a sound of a currently played content in response to a difference between a user's sleep level and a reference level according to a 2nd example of the present disclosure.

Referring to FIG. 17, while a content containing a specific audio is played, the snooze function is activated and the sleep level of the user is determined. In doing so, if the determined sleep level of the user is equal to or lower than the reference level, the controller 180 can end the snooze function and lower the audio volume of the content. If the determined sleep level is higher than the reference level, the controller 180 can stop the audio output of the content or end the playback of the content completely.

In particular, while a user is in a sleep by listening to a music, the snooze function is activated. In doing so, if a sleep level of the user is equal to or lower than a reference level corresponding to a light sleep, the user may be easily awakened from the sleep. Hence, the snooze function is ended. Moreover, when the user is just awakened from the sleep, since the music sound may cause discomfort to the user, the audio volume size of the content is lowered.

On the contrary, if a sleep level of the user is higher than a reference level corresponding to a deep sleep, it indicates a situation that the user is in a deep sleep. Hence, the content audio output, which hinders the deep sleep of the user, is stopped or the playback of the content is completely ended.

For instance, when a volume size of an audio of a currently played content 320 is '5' 324A and a currently determined sleep level of a user is '1st non-REM stage' 323A [FIG. 17 (*a*)], if the sleep level of the user has no change during a predetermined time based on user's bio-information periodically measured by the measuring unit 190, since the '1st non-REM stage' 323A is equal to or lower than a reference level, the controller 180 lowers the volume size '5' 324A of the audio of the content 320 in the '1st non-REM stage' 323A to '3' 324B [FIG. 17 (*b*)].

Moreover, when a volume size of an audio of a currently played content 320 is '7' 324C and a currently determined sleep level of a user is '4th non-REM stage' 323B [FIG. 17 (*c*)], if the sleep level of the user has no change during a predetermined time based on user's bio-information periodically measured by the measuring unit 190, since the '4th non-REM stage' 323B is higher than a reference level, the controller 180 mutes the volume size '7' 324C of the audio of the content 320 in the '4th non-REM stage' 323B into '0' 324D or ends the playback of the content 320 completely [FIG. 17 (*d*)].

Figure 18:
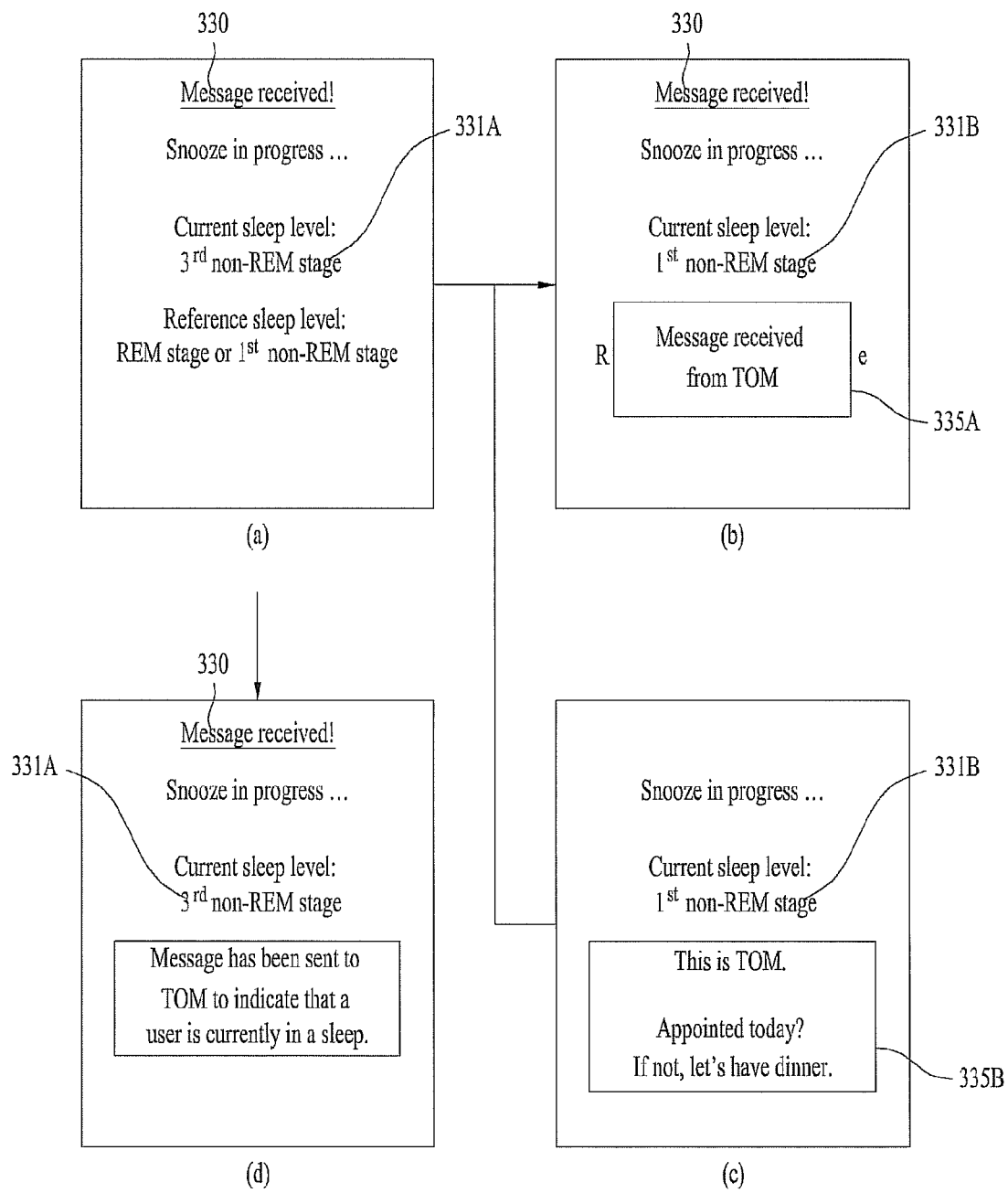
FIG. 18 is a diagram to describe a process for reserving an execution of an occurrence indicating operation of a currently occurring event in accordance with a user's sleep level according to the present disclosure.

Meanwhile, after the snooze function has been activated like the step S180 shown in FIG. 5, if a specific event occurs and a sleep level according to a user's sleep depth is determined like the step S211 shown in FIG. 14, referring to FIG. 18, the controller 180 can lead an operation of indicating an occurrence of the specific event to be performed until the determined sleep level becomes equal to or lower than a reference level.

FIG. 18 is a diagram to describe a process for reserving an execution of an occurrence indicating operation of a currently occurring event in accordance with a user's sleep level according to the present disclosure.

Referring to FIG. 18, after the snooze function has been activated, if a specific event occurs in the terminal 100 and a user's sleep level at a timing point of the occurrence of the specific event is equal to or lower than a reference level, the user may be in a state of a light sleep or is about to wake up from the sleep. Hence, the controller 180 performs an operation of indicating the occurrence of the specific event.

On the contrary, after the snooze function has been activated, if a specific event occurs in the terminal 100 and a user's sleep level at a timing point of the occurrence of the specific event is higher than the reference level, the user is currently in a state of a deep sleep (i.e., a state in which the user hardly wakes up). Although the operation of indicating the specific event is performed, the user can be aware of the occurrence of the specific event after wakeup. Hence, the controller 180 reserves the execution of the specific event occurrence indicating operation until the user's sleep level becomes equal to or lower than the reference level.

In this case, the specific event may include at least one of a call reception, an SMS/MMS message reception, an email reception, an instant message reception, a schedule indication and the like. And, the user can freely set at least one event to reserve the event occurrence indication according to the user's sleep level among the types of the events through a menu manipulation.

For instance, referring to FIG. 18 (*a*), an event of a message reception 330 occurs in the course of operation of the snooze function. And, a user's sleep level determined at the timing point of the occurrence of the event of the message reception 330 is '3rd non-REM stage' 331A. In doing so, referring to FIG. 18 (*b*), if the user's sleep level '3rd non-REM stage' 331A is changed into '1st non-REM stage' 331B equal to or lower than the reference level, the controller 1280 can display an information 335A indicating the occurrence of the event of the message reception 330 on a screen or output an audio indicating the occurrence of the event of the message reception 330.

Moreover, referring to FIG. 18 (*c*), if the user's sleep level '3rd non-REM stage' 331A is changed into the '1st non-REM stage' 331B equal to or lower than the reference level, the controller 1280 can display a content 335B of the received message on the screen.

On the contrary, referring to FIG. 18 (*a*), an event of a message reception 330 occurs in the course of operation of the snooze function. And, a user's sleep level determined at the timing point of the occurrence of the event of the message reception 330 is '3rd non-REM stage' 331A. In doing so, referring to FIG. 18 (*d*), if the user's sleep level '3rd non-REM stage' 331A does not become equal to or lower than the reference level, the controller 1280 can send a message, which indicates that a message check is impossible due to a current state of the user in a sleep, to a terminal of a sender of the message via the wireless communication unit 110.

For another example, while the snooze function is active, when a cell reception event occurs, if a user's sleep level determined at the timing point of the occurrence of the event of the call reception 330 is equal to or lower than the reference level, the controller 180 directly connects the received call.

On the contrary, if the user's sleep level determined at the timing point of the occurrence of the event of the call reception 330 is higher than the reference level, the controller 180 reserves a connection of the received call until the user's sleep level becomes equal to or lower than the reference level. And, the controller 180 can send a message, which indicates that a message check is not possible due to a current state of the user in a sleep, to a terminal of a sender of the message via the wireless communication unit 110.

Figure 19:
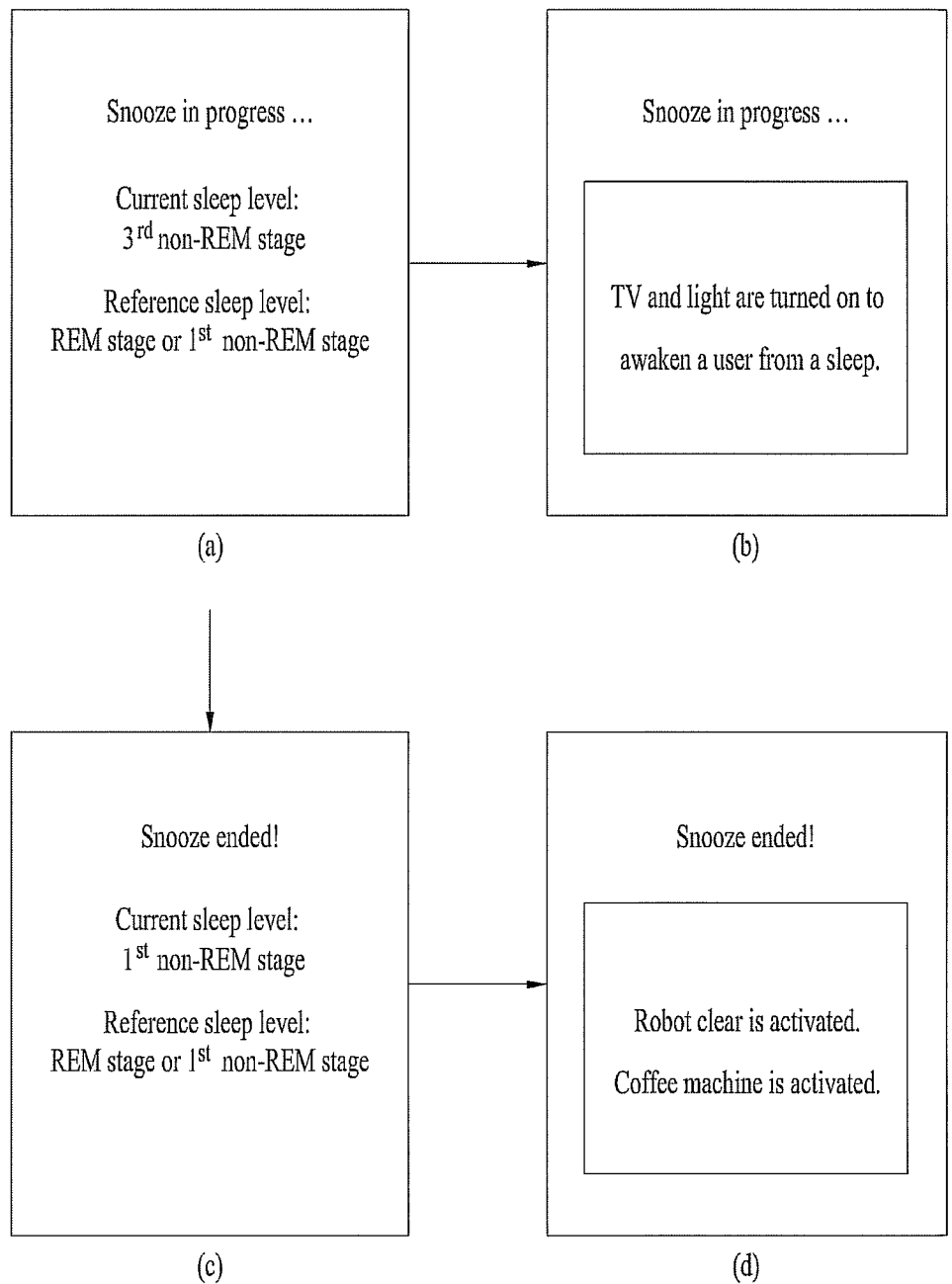
FIG. 19 is a diagram to describe a process for controlling an operation of an external device in the course of an active snooze function or on ending a snooze function according to the present disclosure.

Meanwhile, referring to FIG. 19, if a communication with the terminal 100 is connected while the snooze function is active, the controller 100 can command an external device, of which operation can be controlled by the terminal 100, to perform an operation of awakening a user from a sleep. If the snooze function is ended in response to a sleep level of the user, the controller 180 can command the external device, of which operation can be controlled by the terminal 100, to perform an operation previously set by the user.

FIG. 19 is a diagram to describe a process for controlling an operation of an external device in the course of an active snooze function or on ending a snooze function according to the present disclosure.

Referring to FIG. 19 (*a*), since a sleep level of a user corresponds to the reference level, the snooze function is maintained.

In doing so, referring to FIG. 19 (*b*), while the snooze function is active, the controller 180 transmits a signal for commanding at least one communication-connected external device around the terminal 100 to perform an operation of awakening a user from a sleep, to the at least one external device via the wireless communication unit 110.

In this case, the terminal 100 and the at least one external device are connected to each other via such a short range communication network as DLNA and the like. And, the user can freely set an operation of awakening the user from the sleep in external devices currently communication-connected to the terminal 100 through menu manipulations.

For instance, referring to FIG. 19 (*b*), the terminal 100, a TV and a light are communication-connected to one another. And, a user sets an operation of turning on each of the TV and the light as an operation of awakening a user from a sleep through the menu manipulation.

In particular, if the snooze function is activated, the controller 180 generates a signal for commanding the TV and the light to be turned on and then transmits the command signal generated for turning on the TV and the light to each of the TV and the light via the wireless communication unit 110.

Moreover, since a sleep level of the user is higher than the reference level, if the snooze function is ended [FIG. 19 (*c*)], the controller 180 can transmit a signal for commanding the at least one external device to perform an operation previously set by the user to the at least one external device via the wireless communication unit 110 [FIG. 19 (*d*)].

In particular, the user can freely set operations, which will be performed by external devices currently communication-connected to the terminal 100 when the user wakes up from the sleep, for the external devices through the menu manipulations.

For instance, referring to FIG. 19 (*d*), the terminal 100, a robot cleaner and a coffee machine are communication-connected to one another. And, the user sets an operation of turning on the robot cleaner and an operation of turning on the coffee machine as an operation to be performed by the robot cleaner and an operation to be performed by the coffee machine in case of user's wakeup from a sleep, respectively.

In particular, if the snooze function is ended, the controller 180 generates a signal for commanding the robot cleaner and the coffee machine to be turned on and then transmits the command signal generated for turning on the robot cleaner and the coffee machine to each of the robot cleaner and the coffee machine via the wireless communication unit 110.

Figure 20:
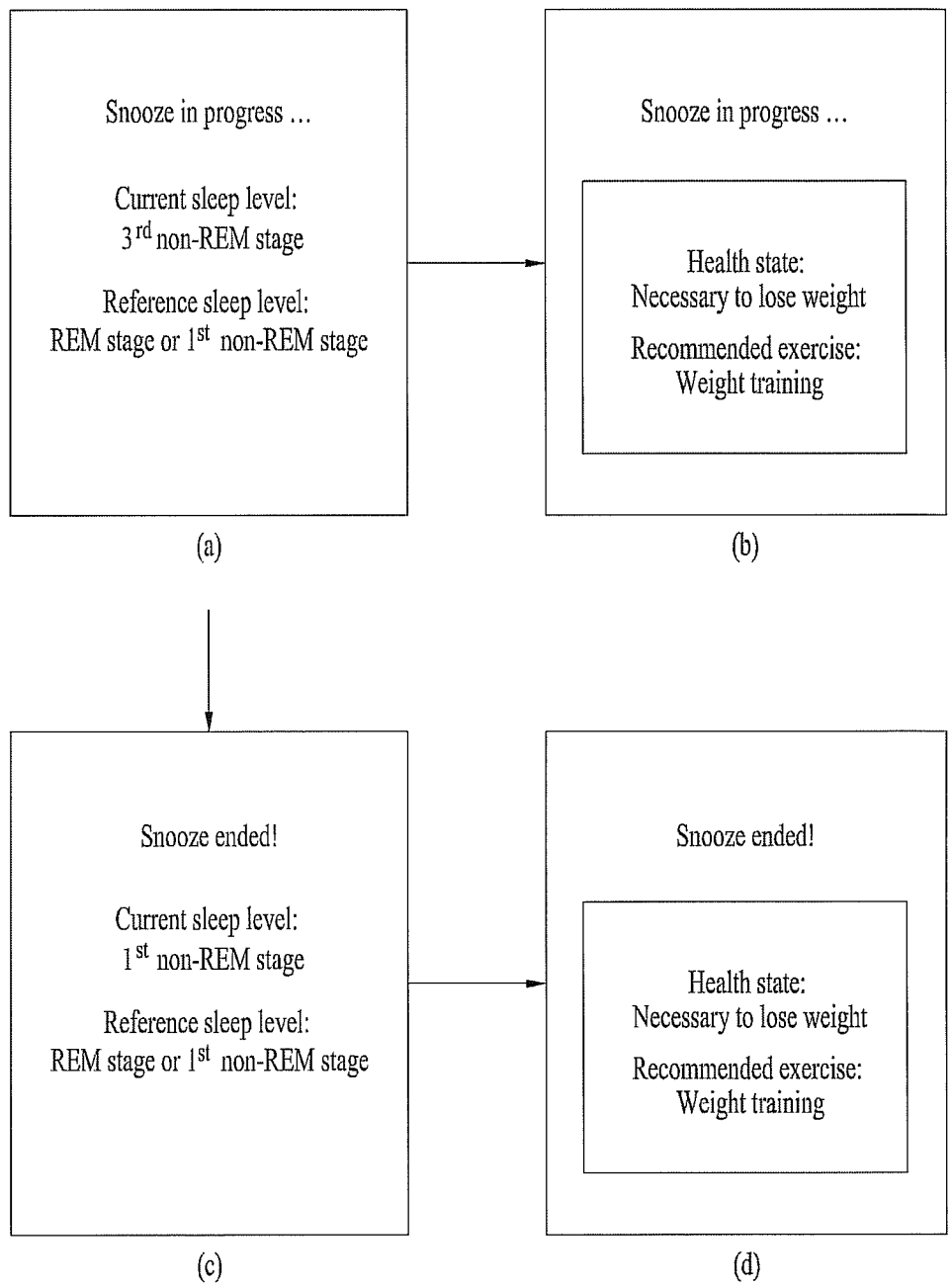
FIG. 20 is a diagram to describe a process for providing a health state information and an exercise information for improvement of a health state based on user's bio-information in the course of an active snooze function or on ending an snooze function according to the present disclosure.

Finally, referring to FIG. 20, after the snooze function has been activated, if bio-information of a user is measured, the controller 180 checks a current health state of the user based on the measured bio-information. The controller 180 is then able to provide the user with an information indicating the checked health state and an exercise information for improvement of the health state (e.g., if the health state is not good) in the course of the active snooze function or after the end of the snooze function.

FIG. 20 is a diagram to describe a process for providing a health state information and an exercise information for improvement of a health state based on user's bio-information in the course of an active snooze function or on ending an snooze function according to the present disclosure.

Referring to FIG. 20 (*a*), since a sleep level of a user corresponds to the reference level, the snooze function is maintained.

In doing so, the controller 180 creates an information indicating a health state of the user based on user's bio-information measured in the course of the active snooze function. In particular, bio-informations corresponding to various health states and exercise informations suitable for the health states or improvements of the health states are saved in the memory 160. Referring to FIG. 20 (*b*), the controller 180 checks that a currently measured bio-information of the user belongs to which one of the health states among the bio-informations corresponding to the health states saved in the memory 160, creates an information indicating the checked health state and a corresponding exercise information, and then displays the created informations.

Alternatively, if the bio-informations indicating the various health states are not saved in the memory 160, the controller 180 transmits the measured bio-information of the user to a website (or server) for a health diagnosis previously set by the user via the wireless communication unit 110. If an information indicating the health state of the user and an exercise information for health improvement are received from the website (or server), the controller 180 can display the received health state information and the received exercise information.

Moreover, referring to FIG. 20 (*c*) and FIG. 20 (*d*), after the snooze function has been ended, the controller 180 can display the user's health state information and the corresponding exercise information created by the step shown in FIG. 20 (*b*).

As broadly described and embodied herein, the embodiments of the present disclosure provide various effects and/or features.

First of all, after an alarm has been outputted, while a user is currently asleep, a snooze function for the alarm is activated based on user's bio-information. Therefore, the present disclosure provides an effect that the user can be fully awakened from the sleep at a user-specific time through the snooze function.

Secondly, after a snooze function has been activated, if a state of a user fully waking up from a sleep is recognized based on user's bio-information, the snooze function is ended. Therefore, the present disclosure facilitates the user to automatically end the snooze function without separate manipulation.

In one embodiment, a mobile terminal may include a sensor configured to sense information associated with a user, a memory to store prescribed alarm settings, an output device to provide an alarm based on the stored alarm settings, and a controller configured to control the alarm based on the sensed information. The controller may control the output device to output the alarm based on the alarm settings, control the sensor to sense the information associated with the user after the alarm is provided, determine whether the sensed information corresponds to a sleep state of the user, and automatically activate a snooze function when the sensed information corresponds to the sleep state.

The sensed information may include at least one of a pulse, a body temperature, data for an electrocardiogram, data for an electromyogram, data for an electroencephalogram, a blood flow or oxygen saturation. The mobile terminal is a wristwatch, and wherein the sensor is provided on a surface of the wristwatch to contact the user's skin. A wireless communication interface may be provided that receives time information associated with a sunrise. The alarm may be set to output based on the received time information while the user is asleep. A light sensor may be provided that measures a level of ambient light, wherein the alarm is set to output when the measured level of light is greater than or equal to a prescribed threshold while the user is asleep.

The controller may set the alarm when the user is asleep. A sensor may be provided that senses a motion of the terminal, wherein the alarm is set to output when an amount of sensed motion is less than or equal to a prescribed threshold while the user is asleep. Moreover, a sensor may be provided that senses acceleration of the terminal, wherein the alarm is set to output when the sensed acceleration of the terminal is greater than or equal to a prescribed threshold while the user is asleep. The alarm may be set to output in response to a prescribed event while the user is asleep, the prescribed event being at least one of a sunrise, a sunset, an amount of ambient light, vital signs of a user, a motion of the mobile terminal, an acceleration of the mobile terminal, or an output from an application program executing on the mobile terminal.

A setting for the snooze function may be stored in the memory, the snooze setting including at least one of a period of time between alarm outputs, a number of times the alarm is output, or a type of sound output during the snooze function, and wherein the snooze setting is changeable after activation of the snooze function. The mobile terminal may further include a motion sensor configured to sense a motion gesture performed on the terminal, and a touchscreen configured to sense a touch gesture. The controller may set or change the at least one of the period of time between alarm output, the number of times the alarm is output, or the type of sound output during the snooze function in response to the motion gesture sensed by the sensor or the touch gesture sensed by the touchscreen.

A display may be provided, wherein when the snooze function is activated, the controller is configured to recognize a current state of health of the user based on the measured information, and wherein the controller controls a display to display at least one of information indicating the recognized state of health or information regarding exercises for improving the recognized state of health. Moreover, after the snooze function has been activated, the controller may control the sensor to sense information associated with the user, determine a sleep state of the user based on the sensed information, and determine whether to end the snooze function based on the recognized sleep state. The controller may also determine a level of sleep corresponding to a level of the sensed information, a lower level of sleep associated with light sleep and a higher level of sleep associated with deep sleep, wherein, when the determined level of sleep is lower than or equal to a reference level, the controller ends the snooze function, and wherein, when the determined sleep level is higher than the reference level, the controller maintains the snooze function.

When the determined level of sleep gets closer to the reference level, the controller may decrease a volume of an alarm for the snooze function, and when the level of sleep gets farther from the reference level, the controller may increase the volume of the alarm for the snooze function. When the snooze function is active while an audio content is being played back, a volume of the audio content may be increased corresponding to an increase in the determined level of sleep and decreased corresponding to a decrease in the determined level of sleep. Moreover, in a case the snooze function is active while an audio content is being played, when the determined level of sleep is lower than or equal to the reference level, the controller may end the snooze function and decreases a volume of the audio content, and when the determined level of sleep is higher than the reference level, the controller may maintain the snooze function and stops playback of the audio content. When a prescribed event is detected while the snooze function is active, the controller may be configured to defer notification of the prescribed event when the determined level of sleep is greater than the reference level.

A wireless communication interface may be coupled to at least one external device, wherein when the controller maintains the snooze function based on the recognized sleep state, the controller controls the at least one external device to output an alarm according to the snooze function, and when the controller ends the snooze function based on the recognized sleep state, the controller controls the at least one external device to perform a previously set operation.

In one embodiment, a method of controlling a mobile terminal may include activating an alarm function based on an alarm setting stored in a memory, determining whether a prescribed condition is satisfied according to the alarm setting, outputting an alarm through an output device in response to the prescribed condition, sensing information associated with a user after the alarm is output, the sensed information corresponding to vital signs of the user, determining whether the sensed information corresponds to a prescribed sleep state based on the sensed information, and automatically activating a snooze function when the sensed information corresponds to the prescribed sleep state.

In one embodiment, a mobile terminal according to the present disclosure may include a measuring unit configured to measure a bio-information of a user, a memory having an alarm set therein, an alarm unit configured to output the alarm, and a controller configured to measure the bio-information of the user through the measuring unit after the outputted alarm, the controller, if determining that the user is currently in a sleep based on the measured bio-information, control a snooze function for the alarm to be automatically activated.

The bio-information may include at least one of a pulse, a body temperature, an electrocardiogram, an electromyogram, an electroencephalogram, a blood flow or an oxygen saturation. The terminal may include a terminal of a wristwatch type and wherein the measuring unit is provided to a surface of the terminal coming in contact with a wrist of the user.

A wireless communication unit may be configured to receive information related to a sunrise time, wherein the alarm is set in the memory to be outputted at the sunrise time received via the wireless communication unit in the course of the sleep of the user. An illumination intensity sensor may be configured to measure a surrounding illumination intensity of the terminal, wherein the alarm is set in the memory to be outputted if the surrounding illumination intensity measured by the illumination intensity sensor is equal to or greater than a threshold in the course of the sleep of the user.

The alarm may be set in the memory to be outputted while the user is in the sleep. A motion sensor may be configured to sense a motion of the terminal, wherein the alarm is set in the memory to be outputted if a motion amount of the terminal sensed by the motion sensor is equal to or smaller than a threshold in the course of the sleep of the user. An acceleration sensor configured to measure an acceleration of the terminal, wherein the alarm is set in the memory to be outputted if the acceleration of the terminal measured by the acceleration sensor is equal to or greater than a threshold in the course of the sleep of the user.

The alarm may be set in the memory to be outputted if a specific event occurs in the course of the sleep of the user. At least one of a snooze repetitive period, a snooze repetitive count or an alarm sound of the snooze function for the alarm is previously set by the user and wherein at least one of the snooze repetitive period, the snooze repetitive count or the alarm sound is changeable by the user after activation of the snooze function. A motion sensor may be configured to sense a motion gesture performed on the terminal and a touchscreen may be configured to sense a touch gesture performed by the user. The controller may set or change at least one of the snooze repetitive period, the snooze repetitive count or the alarm sound in response to the motion gesture sensed by the motion sensor or the touch gesture sensed by the touchscreen.

A display unit may be provided, wherein if the snooze function is activated, the controller may recognize a current health state of the user based on the measured bio-information and wherein the controller controls the display unit to display one of information indicating the checked health state and an exercise information for improvement of the recognized health state. After the snooze function has been activated, the controller may control the measuring unit to measure the bio-information of the user, recognizes a sleep state of the user based on the measured bio-information, and then determines whether to end the activated snooze function based on the recognized sleep state.

The controller may determine a sleep level according to a sleep depth level of the user based on the measured bio-information, wherein if the determined sleep level is equal to or lower than a reference level, the controller ends the snooze function, and wherein if the determined sleep level is higher than the reference level, the controller maintains the snooze function. If the sleep level of the user gets closer to the reference level, the controller may decrease an output strength of an alarm sound of the snooze function and wherein if the sleep level of the user gets farther from the reference level, the controller may increase the output strength of the alarm sound of the snooze function.

After the snooze function has been activated in the course of playing a content containing a specific audio is played, if the sleep level of the user gets closer to the reference level, the controller may decrease an audio volume size of the content and wherein if the sleep level of the user gets farther from the reference level, the controller may increase the audio volume size of the content.

After the snooze function has been activated in the course of playing a content containing a specific audio is played, if the sleep level of the user is equal to or lower than the reference level, the controller may end the snooze function and also decrease an audio volume size of the content. Moreover, if the sleep level of the user is higher than the reference level, the controller may stop an audio output of the content and also maintain the snooze function. After the snooze function has been activated, if a specific event occurs, the controller may reserve an execution of an operation of indicating an occurrence of the specific event until the sleep level of the user becomes equal to or smaller than the reference level.

A wireless communication unit communication-connected to at least one external device may be provided, wherein if determining to maintain the snooze function based on the recognized sleep state, the controller controls the wireless communication unit to transmit a signal for commanding the at least one external device to perform an operation of awakening the user from the sleep to the at least one external device and wherein if determining to end the snooze function based on the checked sleep state, the controller controls the wireless communication unit to transmit a signal for commanding the at least one external device to perform an operation previously set by the user to the at least one external device.

In one embodiment, a method of controlling a terminal may include outputting an alarm, measuring a bio-information of a user after outputting the alarm, determining whether the user is currently in a sleep based on the measured bio-information, and if determining that the user is currently in the sleep, automatically activating a snooze function for the alarm.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A mobile terminal, comprising:
a sensor configured to sense information associated with a user;
a memory to store prescribed alarm settings;
an output device to output an alarm based on the stored alarm settings; and
a controller configured to control the alarm based on the sensed information,
wherein the controller
controls the output device to output the alarm based on the alarm settings,
controls the sensor to sense the information associated with the user after the alarm turns on,
determines whether the sensed information corresponds to a sleep state of the user,
automatically activates a snooze function when the alarm turns off and the sensed information corresponds to the sleep state, and
wherein, in a case the snooze function is active while an audio content is being played, when the determined level of sleep is lower than or equal to the reference level, the controller ends the snooze function and decreases a volume of the audio content, and when the determined level of sleep is higher than the reference level, the controller maintains the snooze function and stops playback of the audio content.

2. The mobile terminal of claim 1, wherein the sensed information includes at least one of a pulse, a body temperature, data for an electrocardiogram, data for an electromyogram, data for an electroencephalogram, a blood flow or oxygen saturation.

3. The mobile terminal of claim 1, wherein the mobile terminal is a wristwatch, and wherein the sensor is provided on a surface of the wristwatch to contact the user's skin.

4. The mobile terminal of claim 1, further including a wireless communication interface that receives time information associated with a sunrise, and wherein the alarm is set to output based on the received time information while the user is asleep.

5. The mobile terminal of claim 1, further including a light sensor that measures a level of ambient light, wherein the alarm is set to output when the measured level of light is greater than or equal to a prescribed threshold while the user is asleep.

6. The mobile terminal of claim 1, wherein the controller sets the alarm when the user is asleep.

7. The mobile terminal of claim 1, further including a sensor that senses a motion of the mobile terminal, wherein the alarm is set to output when an amount of sensed motion is less than or equal to a prescribed threshold while the user is asleep.

8. The mobile terminal of claim 1, further including a sensor that senses acceleration of the mobile terminal, wherein the alarm is set to output when the sensed acceleration of the mobile terminal is greater than or equal to a prescribed threshold while the user is asleep.

9. The mobile terminal of claim 1, wherein the alarm is set to output in response to a prescribed event while the user is asleep, the prescribed event being at least one of a sunrise, a sunset, an amount of ambient light, vital signs of a user, a motion of the mobile terminal, an acceleration of the mobile terminal, or an output from an application program executing on the mobile terminal.

10. The mobile terminal of claim 1, wherein a setting for the snooze function is stored in the memory, the snooze setting including at least one of a period of time between alarm outputs, a number of times the alarm is output, or a type of sound output during the snooze function, and wherein the snooze setting is changeable after activation of the snooze function.

11. The mobile terminal of claim 10, further including
a motion sensor configured to sense a motion gesture performed on the mobile terminal; and
a touchscreen configured to sense a touch gesture,
wherein the controller sets or changes the at least one of the period of time between alarm output, the number of times the alarm is output, or the type of sound output during the snooze function in response to the motion gesture sensed by the sensor or the touch gesture sensed by the touchscreen.

12. The mobile terminal of claim 1, further including
a display, wherein when the snooze function is activated, the controller is configured to recognize a current state of health of the user based on the sensed information, and wherein the controller controls the display to display at least one of information indicating the recognized state of health or information regarding exercises for improving the recognized state of health.

13. The mobile terminal of claim 1, wherein, after the snooze function has been activated, the controller controls the sensor to sense information associated with the user, determines a sleep state of the user based on the sensed information, and determines whether to end the snooze function based on the recognized sleep state.

14. The mobile terminal of claim 13, wherein the controller determines the level of sleep corresponding to a level of the sensed information, a lower level of sleep associated with light sleep and a higher level of sleep associated with deep sleep, wherein, when the determined level of sleep is lower than or equal to the reference level, the controller ends the snooze function, and wherein, when the determined sleep level is higher than the reference level, the controller maintains the snooze function.

15. The mobile terminal of claim 14, wherein, when the determined level of sleep gets closer to the reference level, the controller decreases a volume of an alarm for the snooze function, and when the level of sleep gets farther from the reference level, the controller increases the volume of the alarm for the snooze function.

16. The mobile terminal of claim 14, wherein, when the snooze function is active while an audio content is being played back, the volume of the audio content is increased corresponding to an increase in the determined level of sleep and decreased corresponding to a decrease in the determined level of sleep.

17. The mobile terminal of claim 14, wherein, when a prescribed event is detected while the snooze function is active, the controller is configured to defer notification of the prescribed event when the determined level of sleep is greater than the reference level.

18. The mobile terminal of claim 13, further including a wireless communication interface coupled to at least one external device, wherein when the controller maintains the snooze function based on the recognized sleep state, the controller controls the at least one external device to output an alarm according to the snooze function, and when the controller ends the snooze function based on the recognized sleep state, the controller controls the at least one external device to perform a previously set operation.

19. A method of controlling a mobile terminal, the method comprising:
activating an alarm function based on an alarm setting stored in a memory;
determining whether a prescribed condition is satisfied according to the alarm setting;
outputting an alarm through an output device in response to the prescribed condition;
sensing information associated with a user after the alarm turns on, the sensed information corresponding to vital signs of the user;
determining whether the sensed information corresponds to a prescribed sleep state based on the sensed information;
automatically activating a snooze function when the alarm turns off and the sensed information corresponds to the prescribed sleep state; and
wherein, in a case the snooze function is active while an audio content is being played, when a determined level of sleep is lower than or equal to a reference level, the snooze function is ended and a volume of the audio content is decreased, and when the determined level of sleep is higher than the reference level, the snooze function is maintained and playback of the audio content is stopped.

* * * * *